United States Patent [19]

Dow et al.

[11] Patent Number: 5,767,133
[45] Date of Patent: Jun. 16, 1998

[54] SECONDARY AMINES AS ANTIDIABETIC AND ANTIOBESITY AGENTS

[75] Inventors: Robert L. Dow, Waterford; Stephen W. Wright, Old Lyme, both of Conn.

[73] Assignee: Pfizer Inc., New York, N.Y.

[21] Appl. No.: 569,152

[22] PCT Filed: May 20, 1994

[86] PCT No.: PCT/IB94/00117

§ 371 Date: Dec. 14, 1995

§ 102(e) Date: Dec. 14, 1995

[87] PCT Pub. No.: WO94/29290

PCT Pub. Date: Dec. 22, 1994

[51] Int. Cl.$^6$ .................... A61K 31/44; C07D 401/12
[52] U.S. Cl. .................... 514/339; 546/278.1; 548/181; 548/491; 548/113; 544/333
[58] Field of Search .................... 546/278.1; 514/339, 514/256, 365, 415; 544/333; 548/181, 491

[56] References Cited

U.S. PATENT DOCUMENTS

| | | | |
|---|---|---|---|
| 4,309,443 | 1/1982 | Smith et al. | 424/319 |
| 4,341,793 | 7/1982 | Ferris | 424/279 |
| 4,382,958 | 5/1983 | Duckworth | 424/330 |
| 4,396,627 | 8/1983 | Ainsworth et al. | 424/309 |
| 4,410,539 | 10/1983 | Cross | 424/273 R |
| 4,432,993 | 2/1984 | Ferris | 424/285 |
| 4,478,849 | 10/1984 | Ainsworth et al. | 424/285 |
| 4,654,371 | 3/1987 | Ainsworth et al. | 514/555 |
| 4,882,433 | 11/1989 | Johnson | 546/273 |
| 4,886,814 | 12/1989 | Reiffen et al. | 514/326 |
| 5,061,727 | 10/1991 | Bloom et al. | 514/465 |
| 5,106,867 | 4/1992 | Bloom | 514/465 |
| 5,153,210 | 10/1992 | Ainsworth | 514/369 |

FOREIGN PATENT DOCUMENTS

| | | |
|---|---|---|
| 0254532A1 | 1/1988 | European Pat. Off. . |
| 0427480A1 | 5/1991 | European Pat. Off. . |
| 0455006A2 | 11/1991 | European Pat. Off. . |
| 08165276 | 6/1996 | Japan . |

OTHER PUBLICATIONS

E.J. Corey et al.: "A Stable and Easily Prepared Catalyst for the Eenantioselective Reduction of Ketones. Applications to Multistep Syntheses", *J. Am. Chem. Soc.* 1987, 109, 7925–7926.

Janice M. Klunder et al.: "Arenesulfonate Derivatives of Homochiral Glycidol: Versatile Chiral Building Blocks for Organic Synthesis", *J. Org. Chem.*, 1989, 54, 1295–1304.

L. René et R. Royer: "Recherches sur le benzofuranne", *Bulletin De La Societe Chimique De France*, 1971, 12, 4329–4331.

Ahmed F. Abdel-Magid et al.: "Reductive Amination of Aldehydes and Ketones by Using Sodium Triacetoxyborohdride." *Tetrahedron Letters*, 1990, 31, 5595–5598.

Randall K. Atkins et al.: "Alkylation of N–Trimethylsilylated Primary Amines with Arylethylene Oxides. An Efficient Synthesis of 1–Phenethanolamines", *Tetrahedron Letters*, 1986, 27, 2451–2454.

C. J. Swain et al.: "Novel 5–HT$_3$ Antagonists. Indole Oxadiazoles", *J. Med. Chem.*, 1991, 34, 140–151.

Shishue Chiou and Henry J. Shine: "A Simplified Procedure for Preparing 3,5–Disubstituted–1,2,4–Oxadiazoles by Reaction of Amidoximes with Acyl Chlorides in Pyridine Solution", *J. Heterocyclic Chem.*, 1989, 26, 125.

David E. Nichols et al.: "Asymmetric Synthesis of Psychotomimetic Phenylisopropylamines", *J. Med. Chem.*, 1973, 16, 480–483.

Masanori Kosugi et al.: "A New Palladium Catalyzed Aromatic Acetonylation by Acetonyltributyltin", *Chemistry Letters*, 1982, 16, 939–940.

Gary N. Barber$^1$ and R. A. Olofson: "A Useful, Regiospecific Synthesis of Isoxazoles", *J. Org. Chem.*, 1978, 43, 3015.

Ralph Howe et al.: "Selective β$_3$–Adrenergic Agonists of Brown Adipose Tissue and Thermogenesis. 2.[4–[2–[(2–Hydroxy–3–phenoxypropyl)amino]ethoxy]phenoxy]–acetamides", *J. Med. Chem.*, 1992, 35, 1759–1764.

David C. Humber et al.: "(R,R)–5–[2–[[2–(3–Chlorophenyl)–2–hydroxy–3benzodioxole–2,2–dicarboxylate (CL 316,243). A Potent β–Adrenergic Agonist Virtually Specific for β$_3$ Receptors", *J. Med. Chem.*, 1992, 35, 3081–3084.

Ralph Howe et al.: "Selective β$_3$Adrenergic Agonists of Brown Adipose Tissue and Thermogenesis. 1 [4–[–[(2–Hydroxy–3–phenoxypropyl)amino]ethoxy]phenoxy]– acetates", *J. Med. Chem.*, 1992, 35, 1751–1759.

*Primary Examiner*—C. Warren Ivy
*Assistant Examiner*—Charandit S. Aulakh
*Attorney, Agent, or Firm*—Peter C. Richardson; Gregg C. Benson; Robert T. Ronau

[57] ABSTRACT

The present invention relates to compounds of the formula

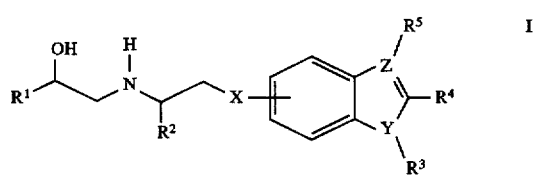

having utility as hypoglycemic and antiobesity agents, methods for their use and pharmaceutical compositions containing them. The compounds of the present invention also possess utility for increasing lean meat deposition and/or improving lean meat to fat ratio in edible animals, i.e. ungulate animals and poultry.

52 Claims, No Drawings

SECONDARY AMINES AS ANTIDIABETIC AND ANTIOBESITY AGENTS

This application is a 371 of PCT/IB9,400,117, which is now published as WO94/29290 on Dec. 22, 1994.

BACKGROUND OF THE INVENTION

The present invention relates to certain compounds of the formula (I) depicted below, having utility as hypoglycemic and antiobesity agents, methods for their use and pharmaceutical compositions containing them. The compounds of the present invention also possess utility for increasing lean meat deposition and/or improving the lean meat to fat ratio in edible animals, i.e. ungulate animals and poultry.

The disease diabetes mellitus is characterized by metabolic defects in production and utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The compounds of the present invention and the pharmaceutically active salts thereof effectively lower blood glucose levels when administered orally to mammals with hyperglycemia or diabetes.

The compounds of the present invention also decrease weight gain when administered to mammals. The ability of these compounds to affect weight gain is due to activation of β-adrenergic receptors which stimulate the metabolism of adipose tissue.

β-Adrenergic receptors can be divided into $\beta_1$, $\beta_2$ and $\beta_3$-subtypes. Activation of $\beta_1$-receptors invokes increases in heart rate while activation of $\beta_2$-receptors induces relaxation of smooth muscle tissue which produces a drop in blood pressure and the onset of smooth muscle tremors. Activation of $\beta_3$-receptors stimulates lipolysis (the breakdown of adipose tissue triglycerides to glycerol and free fatty acids), and thereby promotes the loss of fat mass. Compounds that stimulate $\beta_3$-receptors will have anti-obesity activity. In addition, compounds which are $\beta_3$-adrenoceptor agonists have hypoglycemic or anti-diabetic activity, but the mechanism of this effect is unknown. A compound that selectively stimulates $\beta_3$-receptors, i.e., has little or no $\beta_1$ or $\beta_2$-activity, will have the desired anti-diabetic and/or anti-obesity activity, but without the undesirable effects of increased heart rate ($\beta_1$-effect) or muscle tremor ($\beta_2$-effect). The use of $\beta_3$-adrenoceptor agonists as antidiabetic, hypoglycemic and antiobesity agents has been frustrated, however, by the lack of selectivity of these agents for $\beta_3$-adrenoceptors over the other two other adrenoceptors, $\beta_1$, and $\beta_2$. The compounds of the present invention are selective $\beta_3$ adrenoceptor agonists.

SUMMARY OF THE INVENTION

The present invention relates to compounds of the formula

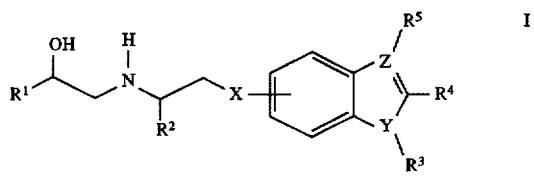

wherein $R^1$ is phenyl, —$(CH_2)_n$—O-phenyl, pyridyl, pyrimidyl or thiazolyl; wherein said phenyl and the phenyl moiety of said —$(CH_2)_n$—O-phenyl may optionally be substituted with one or more substituents independently selected from hydrogen, $(C_1-C_6)$alkyl optionally substituted with one or more halo atoms, hydroxy, $(C_1-C_6)$alkoxy optionally substituted with one or more halo atoms, $(C_1-C_6)$alkylthio, fluoro, chloro, bromo, iodo, nitro, amino, —$NR^7R^8$ and cyano; and wherein each of the ring carbon atoms of said pyridyl, pyrimidinyl or thiazolyl may optionally be substituted with a substituent independently selected from hydrogen, $(C_1-C_6)$alkyl optionally substituted with one or more halo atoms, hydroxy, $(C_1-C_6)$alkoxy optionally substituted with one or more halo atoms, $(C_1-C_6)$alkylthio, fluoro, chloro, bromo, iodo, nitro, amino, —$NR^7R^8$ and cyano;

$R^2$ is hydrogen or $(C_1-C_6)$alkyl optionally substituted with one or more halo atoms;

$R^3$ is hydrogen, —$(CH_2)_n$-phenyl, —$(C_1-C_{10})$alkyl, —$(CH_2)_n$—$NR^7R^8$, —$(CH_2)_n$—$CO_2R^2$,

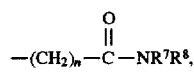

—$(CH_2)_n$—$OR^2$, —$(CH_2)_n$—$SO_3R^2$, —$(CH_2)_n$—$SO_2$—$(C_1-C_6)$alkyl, —$(CH_2)_n$—$SO_2NR^7R^8$, or a heterocycle selected from —$(CH_2)_n$-pyridyl, —$(CH_2)_n$-pyrimidyl, —$(CH_2)_n$-pyrazinyl, —$(CH_2)_n$-isoxazolyl, —$(CH_2)_n$-oxazolyl, —$(CH_2)_n$-thiazolyl, —$(CH_2)_n$-(1,2,4-oxadiazolyl), —$(CH_2)_n$-imidazolyl, —$(CH_2)_n$-triazolyl and —$(CH_2)_n$-tetrazolyl; wherein one of the ring nitrogen atoms of said —$(CH_2)_n$-imidazolyl, —$(CH_2)_n$-triazolyl and —$(CH_2)_n$-tetrazolyl may optionally be substituted by $(C_1-C_6)$alkyl optionally substituted with one or more halo atoms; wherein each of said heterocycles may optionally be substituted on one or more of the ring carbon atoms by respectively, one or more substituents independently selected from $(C_1-C_6)$alkyl optionally substituted with one or more halo atoms, halo, nitro, cyano, —$(CH_2)_n$—$NR^7R^8$, —$(CH_2)_n$—$CO_2R^2$,

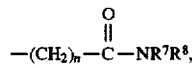

—$(CH_2)_n$—$OR^2$, —$(CH_2)_n$—$SO_2R^2$, —$(CH_2)_n$—$SO_2$—$(C_1-C_6)$alkyl, or —$(CH_2)_n$—$SO_2NR^7R^8$; wherein the phenylmoiety of said —$(CH_2)_n$-phenyl may optionally be substituted with one or more substituents, independently selected from $(C_1-C_6)$alkyl optionally substituted with one or more halo atoms, hydroxy, $(C_1-C_6)$alkoxy optionally substituted with one or more halo atoms, $(C_1-C_6)$alkylthio, fluoro, chloro, bromo, iodo, cyano, nitro, —$(CH_2)_n$—$NR^7R^8$, —$(CH_2)_n$—$CO_2R^2$,

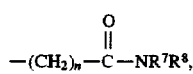

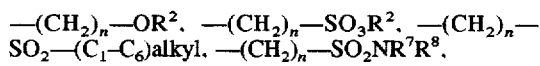

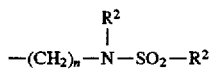

wherein each $R^2$ is selected independently of the other $R^2$ and

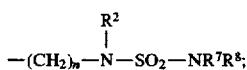

$R^4$ is —$(CH_2)_n$—CN, —$(CH_2)_nCO_2R^2$, —$(CH_2)_n$—$SO_3R^2$, —$(CH_2)_n$—$SO_2$—$(C_1$–$C_6)$alkyl, —$(CH_2)_n$—$SO_2$—$NR^7R^8$, —$(CH_2)_nCH_2OH$ optionally substituted with a suitable protecting group, —$(CH_2)_n$—CHO, —$(CH_2)_n$—C(=O)$R^2$, —$(CH_2)_n$—C(=O)$NR^7R^8$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4oxadiazolyl, —$(CH_2)_n$-isoxazolyl, —$(CH_2)_n$-tetrazolyl and —$(CH_2)_n$-pyrazolyl; wherein one of the ring nitrogen atoms of said —$(CH_2)_n$-imidazolyl, —$(CH_2)_n$-triazolyl and —$(CH_2)_n$-tetrazolyl may optionally be substituted by $(C_1$–$C_6)$alkyl optionally substituted with one or more halo atoms; wherein each of said heterocycles may optionally be substituted on one or more of the ring carbon atoms by respectively, one or more substituents independently selected from hydrogen, $(C_1$–$C_6)$alkyl optionally substituted with one or more halo atoms, —$(CH_2)_n$—$NR^7R^8$, —$(CH_2)_n$—$CO_2R^2$, halo, nitro, cyano,

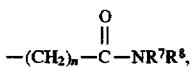

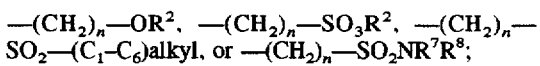

$R^5$ is hydrogen or $(C_1$–$C_6)$alkyl optionally substituted with one or more halo atoms;

$R^7$ and $R^8$ are independently hydrogen, $(C_1$–$C_6)$alkyl optionally substituted with one or more halo, $(C_1$–$C_8)$alkoxy($C_1$–$C_6$)alkyl or $(C_3$–$C_8)$cycloalkyl, or $R^7$ and $R^8$, together with the nitrogen to which they are attached, form a saturated heterocyclic ring having from 3 to 7 carbon atoms wherein one of said carbon atoms may optionally be replaced by oxygen, nitrogen or sulfur;

n is an integer from zero to six;

X is a direct link, oxygen or sulfur;

Y is oxygen, nitrogen or sulfur; and

Z is carbon or nitrogen; with the proviso that: (a) when Y is oxygen or sulfur, $R^3$ is absent, and (b) when Z is nitrogen, $R^5$ is absent;

or a pharmaceutically acceptable pro-drug of such compound, or a pharmaceutically acceptable salt of such compound or pro-drug.

Preferred compounds of formula I are those wherein $R^1$ is —$(CH_2)_n$-O-phenyl optionally substituted with one or more substituents independently selected from hydrogen, $(C_1$–$C_6)$ alkyl optionally substituted with one or more halo atoms, hydroxy, $(C_1$–$C_6)$alkoxy, $(C_1$–$C_6)$alkylthio, amino, fluoro, chloro, bromo and iodo.

Other preferred compounds of formula I are those wherein $R^1$ is phenyl optionally substituted with one or more substituents independently selected from hydrogen, $(C_1$–$C_6)$ alkyl optionally substituted with one or more halo atoms, hydroxy, $(C_1$–$C_6)$alkoxy optionally substituted with one or more halo atoms, $(C_1$–$C_6)$alkylthio, amino, fluoro, chloro, bromo and iodo.

Other preferred compounds of formula I are those wherein $R^1$ is pyridyl wherein one or more of the ring carbon atoms may independently be substituted with hydrogen, $(C_1$–$C_6)$alkyl optionally substituted with one or more halo atoms, hydroxy, $(C_1$–$C_6)$alkoxy optionally substituted with one or more halo atoms, $(C_1$–$C_6)$alkylthio, amino, fluoro, chloro, bromo and iodo.

Other preferred compounds of formula I are those wherein $R^1$ is phenyl, —$(CH_2)$-O-phenyl or pyridyl; wherein said phenyl and the phenyl moiety of said —$(CH_2)_n$- O-phenyl may optionally be substituted with one or more substituents; wherein one or more of the carbon atoms of said pyridyl may optionally be substituted; and wherein said substituents are independently halogen, amino or hydroxy.

Other preferred compounds of formula I are those wherein X is oxygen.

Other preferred compounds of formula I are those wherein X is a direct link.

Other preferred compounds of formula I are those wherein, wherein $R^4$ is —$CO_2CH_3$, —$CO_2H$, —C(=O)$CH_3$, nitrile (—C≡N), or a heterocycle selected from 3-1,2,4-oxadiazolyl, 5-methyl-1,2,4-oxadiazolyl, 3-isoxazolyl, 3-5-methyl-isoxazolyl, 4-(2-methyl(thiazolyl)), 3-methyl-1,2,4-oxadiazolyl and 5-1,2,4-oxadiazolyl.

Other preferred compounds of formula I are those wherein, wherein $R^4$ is —$CO_2R^2$.

Other preferred compounds of formula I are those wherein, wherein Y is nitrogen.

More preferred compounds of formula I are those wherein, wherein Y is nitrogen and $R^3$ is hydrogen, methyl, ethyl, phenylmethyl, pyridylmethyl, pyrizinylmethyl or pyrimidylmethyl.

More preferred compounds of formula I are those wherein $R^3$ is hydrogen, methyl, ethyl, phenylmethyl, pyrimidylmethyl, pyrizinylmethyl or pyridiylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by

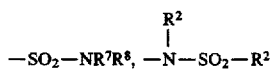

wherein each $R^2$ is selected independently of the other $R^2$ and

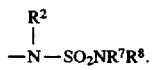

Examples of more preferred compounds of formula I are:

1-(5-(2(2(S)-hydroxy-3-phenoxy-propylamino)-ethoxy)-benzofuran-2-yl)-thanone, 1-(2-(2-isoxazol-3-yl-benzofuran-5-yloxy)-ethylamino)-3-phenoxy-propan-2(S)-ol, 1-(2-(2-(5-methyl-isoxazol-3-yl)-benzofuran-5-yloxy)-ethylamino)-3phenoxy-propan-2(S)-ol, 1-(2-(2-(2-methyl-thiazol4-yl)-benzofuran-5-yloxy)-ethylamino)-3-phenoxy-propan-2(S)-ol, 1-(2-(2-(5-methyl-(1,2,4)-oxadiazol-3-yl)-benzofuran-5-yloxy)-ethylamino)-3-phenoxy-propan-2(S)-ol, 1-(2-(2-(1,2,4)-oxadiazol-3-yl)-benzofuran-5-yloxy)-ethylamino)-3-phenoxy-propan-2(S)-ol, 1-benzyl-5-(2(R)-(2-(3-chloro-phenyl)-2(R)-hydroxy-ethylamino)-propyl)-1H-indole-2-carboxylic acid methyl ester, hydrochloride salt, 1-benzyl-5-(2(R)-(2-(3-chloro-phenyl)-2(R)-hydroxy-ethylamino)-propyl)-1H-indole-2-carboxylic acid, 1-benzyl-5-(2(R,S)-(2(S)-hydroxy-3-phenoxy-propylamino)-propyl)-1H-indole-2-carboxylic acid ethyl ester, 1-benzyl-5-(2(R,S)-(2S)-hydroxy-3-phenoxy-propylamino)-propyl)-1H-indole-2-carboxylic acid, 5-(2(R,S)-(2-(3-chloro-phenyl)-2(R)-hydroxy-ethylamino)-propyl)-1-(4-dimethylsulfamoyl-benzyl)-1H-indole-2-carboxylic acid ethyl ester, 5-(2-(R,S)(2-(3-chloro-phenyl)-2(R)-hydroxy-ethylamino)-propyl)-1-(4-dimethylsulfamoyl-benzyl)-1H-indole-2-carboxylic acid, 1-(4dimethylsulfamoyl-benzyl)-5-(2(R,S)-(2(S)-hydroxy-3-phenoxy-propylamino)-propyl)-1H-indole-2-carboxylic acid ethyl ester, 1-(4-dimethylsulfamoyl-benzyl)-5-(2(R,S)-(2(S)-hydroxy-3-phenoxy-propylamino)-propyl)-1H-indole-2-carboxylic acid, 5-(2(R,S)-(2-(3-chloro-phenyl)-2(R)-hydroxy-ethylamino)-propyl)-1-(4-methanesulfonylamino-benzyl)-1H-indole-2-carboxylic acid ethyl ester, hydrochloride salt, 5-(2(R,S)-(2-(3-chloro-phenyl)-2(R)-hydroxy-ethylamino)-propyl)-1-(4-methanesulfonylamino-benzyl)-1H-indole-2-carboxylic acid, 5-(2(R,S)-(2(S)-hydroxy-3-phenoxy-propylamino)-propyl)-1-(4-methanesulfonylamino-benzyl)-1H-indole-2-carboxylic acid ethyl ester, hydrochloride salt, 5-(2(R,S)-(2(S)-hydroxy-3-phenoxy-propylamino)-propyl)-1-(4-methanesulfonylamino-benzyl)-1H-indole-2-carboxylic acid, 5-(2(R, S)-(2(R, S)-(6-amino-pyridin-3-yl)-2-hydroxy-ethylamino)-propyl)-1-benzyl-H-indole-2-carboxylic acid ethyl ester, 5-(2(R,S)-(2(R,S)-(6-amino-pyridin-3-yl)-2-hydroxy-ethylamino)-propyl)-1-benzyl-1H-indole-2-carboxylic acid hydrochloride salt.

Examples of other preferred compounds of formula I are:

methyl 5-(2-(2(S)-hydroxy-3-phenoxy-propylamino)ethoxy)-benzofuran-2-carboxylic acid, methyl 5-(2(R)-(2-(2-trifluoromethyl-thiazol-4-yl)-2(R)-hydroxyethyl-amino)-propyl)-benzofuran-2-carboxylic acid, 5-(2-(2(S)-hydroxy-3-phenoxy-propylamino)ethoxy)-benzofuran-2-carboxylic acid, 5-(2-(2(S)-hydroxy-3-phenoxy-propylamino)ethoxy)-benzofuran-2-carboxylic acid, (2-methoxy-ethyl)-amide, isopropyl 5-(2-(2(S)-hydroxy-3-phenoxy-propylamino)ethoxy)-benzofuran-2-carboxylic acid, 2-bromo- 1-(5-methoxy-benzofuran-2-yl)ethanone, methyl 5-(2-(2(S)-hydroxy-3-(2-chlorophenoxy)-propylamino)ethoxy)-benzofuran-2-carboxylic acid, methyl 6-(2-(2(S)-hydroxy-3-phenoxy-propylamino)ethoxy)-benzofuran-2-carboxylic acid, 6-(2-(2(S)-hydroxy-3-phenoxy-propylamino)ethoxy)-benzofuran-2-carboxylic acid, methyl 5-(2-(2-(3-chloro-phenyl)-2(R)-hydroxy-ethylamino)-ethoxy)-benzofuran-2-carboxylic acid, 5-(2-(2-(3-chloro-phenyl)-2(R)-hydroxy-ethylamino)-ethoxy)-benzofuran-2-carboxylic acid, methyl 6-(2-(2-(3-chloro-phenyl)-2(R)-hydroxy-ethylamino)-ethoxy)-benzofuran-2-carboxylic acid, methyl 5-(2-(2-(2-trifluoromethyl-thiazol-4-yl)-2(R)-hydroxy-ethylamino)-ethoxy)-benzofuran-2-carboxylic acid, 5-(2-(2-(2-trifluoromethyl-thiazol-4-yl)-2(R)-hydroxy-ethylamino)-ethoxy)-benzofuran-2-carboxylic acid, 1-(5-(2(2(S)-hydroxy-3-phenoxy-propylamino)-ethoxy)-benzofuran-2-yl)-ethanone, 1-(5-(2(2(S)-hydroxy-3-phenoxy-propylamino)-ethoxy)-benzofuran-2-yl)-butanone, 1-(2-(2-isoxazol-3-yl-benzofuran-5-yloxy)-ethylamino)-3-phenoxy-propan-2(S)-ol, 1-(2-(2-isoxazol-3-yl-benzofuran-5-yloxy)-ethylamino)-3-(2-chloro-phenoxy)-propan-2(S)-ol, 1-(2-(2-(5-methyl-isoxazol-3-yl)-benzofuran-5-yloxy)-ethylamino)-3-phenoxy-propan-2(S)-ol, 1-(2-(2-(5-methyl-isoxazol-3-yl)-benzofuran-5-yloxy)-ethylamino)-3-(2-chloro-phenoxy)-propan-2(S)-ol, 1-(2-(2-(5-methyl-isoxazol-3-yl)-benzofuran-5-yloxy)-ethylamino)-3-(2-fluoro-phenoxy)-propan-2(S)-ol, 1-(2-(2-isoxazol-3-yl-benzofuran-5-yloxy)-ethylamino)-3-(2-trifluoromethyl-phenoxy)-propan-2(S)-ol, 1-(2-(2-isoxazol-3-yl-benzofuran-5-yloxy)-ethylamino)-3-(2-cyano-phenoxy)-propan-2(S)-ol, 1-(2-(2-isoxazol-3-yl-benzofuran-5-yloxy)-ethylamino)-3-(2-fluoro-phenoxy)-propan-2(S)-ol, 1(R)-(3-chloro-phenyl)-2-(2-(2-isoxazol-3-yl-benzofuran-5-yloxy)-ethylamino)-ethanol, 1(R)-(3-trifluoromethyl-phenyl)-2-(2-(2-isoxazol-3-yl-benzofuran-5-yloxy)-ethylamino)-ethanol, 1(R)-(3-chloro-phenyl)-2-(2-(2-(5-methyl-isoxazol-3-yl)-benzofuran-5-yloxy)-ethylamino)-ethanol, 1(R)-(3-trifluoromethyl-phenyl)-2-(2-(2-(5-methyl-isoxazol-3-yl)-benzofuran-5-yloxy)-ethylamino)-ethanol, 1(R)-(3-chloro-phenyl)-2-(2-(2-(2-methyl-thiazol-4-yl)-benzofuran-5-yloxy)-ethylamino)-ethanol, 1-(2-(2-(5-methyl-(1,2,4)-oxadiazol-3-yl)-benzofuran-5-yloxy)-ethylamino)-3-(2-chloro-phenoxy)-propan-2(S)-ol, 1-(2-(2-(5-methyl-(1,2,4)-oxadiazol-3-yl)-benzofuran-5-yloxy)-ethylamino)-3-(2-fluoro-phenoxy)-propan-2(S)-ol, 1-(2-(2-(5-trifluoromethyl-(1,2,4)-oxadiazol-3-yl)-benzofuran-5-yloxy)-ethylamino)-3-phenoxy-propan-2(S)-ol, 1-(2-(2-(5-trifluoromethyl-(1,2,4)-oxadiazol-3-yl)-benzofuran-5-yloxy)-ethylamino)-3-(2-chloro-phenoxy)-propan-2(S)-ol, 1-(2-(2-(5-trifluoromethyl-(1,2,4)-oxadiazol-3-yl)-benzofuran-5-yloxy)-ethylamino)-3-(2-fluoro-phenoxy)-propan-2(S)-ol, 1-(2-(2-(5-ethyl-(1,2,4)-oxadiazol-3-yl)-benzofuran-5-yloxy)-ethylamino)-3-phenoxy-propan-2(S)-ol, 1-(2-(2-(5-(2-propyl)-(1,2,4)-oxadiazol-3-yl)-benzofuran-5-yloxy)-ethylamino)-3-phenoxy-propan-2(S)-ol, 1-(2-(2-(5-(2-phenyl)-(1,2,4)-oxadiazol-3-yl)-benzofuran-5-yloxy)-ethylamino)-3-phenoxy-propan-2(S)-ol, 1-(2-(2-(5-(2-(3-pyridyl))-(1,2,4)-oxadiazol-3-yl)-benzofuran-5-yloxy)-ethylamino)-3-phenoxy-propan-2(S)-ol, 1-(2(2-(1,2,4)-oxadiazol-3-yl)-benzofuran-5-yloxy)-ethylamino)-3-(2-chloro-phenoxy)-propan-2(S)-ol, 1-(2-(2-(1,2,4)-oxadiazol-3-yl)-benzofuran-5-yloxy)-ethylamino)-3-(2-fluoro-phenoxy)-propan-2(S)-ol, 1(R)-(3-chloro-phenyl)-2-(2-(2-(5-methyl-(1,2,4)-oxadiazol-3-yl)-benzofuran-5-yloxy)-ethylamino)-ethanol, 1(R)-(3-trifluoro-phenyl)-2-(2-(2-(5-methyl-(1,2,4)-oxadiazol-3-yl)-benzofuran-5-yloxy)-ethylamino)-ethanol, 1(R)-(2-trifluoromethyl-thiazol-4-yl)-2-(2-(2-(5-methyl-(1,2,4)-oxadiazol-3-yl)-benzofuran-5-yloxy)-ethylamino)-ethanol, 1(R)-(3-chloro-phenyl)-2-(2-(2-(5-trifluoromethyl-(1,2,4)-oxadiazol-3-yl)-benzofuran-5-yloxy)-ethylamino)-ethanol, 1(R)-(3-chloro-phenyl)-2-(2-(2-(5-(2-propyl)-(1,2,4)-oxadiazol-3-yl)-benzofuran-5-yloxy)-ethylamino)-ethanol, 1(R)-(3-chloro-phenyl)-2-(2-(2-(1,2,4)-oxadiazol-3-yl-benzofuran-5-yloxy)-ethylamino)-ethanol, 5-(2-(2(S)-hydroxy-3-phenoxy-propylamino)ethoxy)-benzofuran-2-carboxylic acid, 1-propyl-amide, (5-(2-(2(S)-hydroxy-3-phenoxy-propylamino)ethoxy)-benzofuran-2-yl)-pyrrolidin-1-yl-methanone, (5-(2-(2(S)-hydroxy-3-(2-chloro-phenoxy)-propylamino)ethoxy)-benzofuran-2-yl)-pyrrolidin-1-yl-methanone, (5-(2-(2(S)-hydroxy-3-phenoxy-propylamino)ethoxy)-indol-2-yl)-pyrrolidin-1-yl-methanone, (1-methyl-5-(2-(2(S)-hydroxy-3-phenoxy-propylamino)ethoxy)-indol-2-yl)-pyrrolidin-1-yl-methanone, 5-(2-(2-(3-chloro-phenyl)-2(R)-hydroxy-ethylamino)-ethoxy)-benzofuran-2-yl)-pyrrolidin-1-yl-methanone, 5-(2(R,S)-(2-(2-trifluoromethyl-thiazol-4-yl)-2(S)-hydroxy-ethylamino)-propyl)-benzofuran-2-carboxylic acid, 5-(2(R)-(2-(2-trifluoromethyl-thiazol-4-yl)-2(S)-hydroxy-ethylamino)-propyl)-benzofuran-2-carboxylic acid, 4-(2(R,S)-(2-(2-trifluoromethyl-thiazol-4-yl)-2(S)-hydroxy-ethylamino)-propyl)-benzo-furan-2-carboxylic acid, 4-(2(R,S)-(2-(2-trifluoromethyl-thiazol-4-yl)-2(S)-hydroxy-ethylamino)-propyl)-benzo-furan-2-carboxylic acid, 5-(2(R,S)-(2-(3-chloro-phenyl)-2(R)-hydroxy-ethylamino)-propyl)-1H-indole-2-carboxylic acid ethyl ester, 5-(2(R,S)-(2-(3-chloro-phenyl)-2(R)-hydroxy-ethylamino)-propyl)-1H-indole-2-carboxylic acid, 5-(2(R,S)-(2(S)-hydroxy-3-phenoxy-propylamino)-propyl)-1H-indole-2-carboxylic acid, 5-(2(R,S)-(2-(3-chloro-phenyl)-2(R)-hydroxy-ethylamino)-propyl)-1-methyl-1H-indole-2-carboxylic acid ethyl ester, 5-(2(R,S)-(2-(3-chloro-phenyl)-2(R)-hydroxy-ethylamino)-propyl)-1-methyl-1H-indole-2-carboxylic acid, 5-(2(R, S)-(2(S)-hydroxy-3-phenoxy-propylamino)-propyl)-1-methyl-1H-indole-2-carboxylic acid, 5-(2(R)-(2-(3-chloro-phenyl)-2(R)-hydroxy-ethylamino)-propyl)-1-cyclopropylmethyl-1H-indole-2-carboxylic acid methyl ester, 5-(2(R)-(2-(3-chloro-phenyl)-2(R)-hydroxy-ethylamino)-propyl)-1-cyclopropylmethyl-1H-indole-2-carboxylic acid, 1-(3-carboxy-benzyl)-5-(2(R)-(2-(3-chloro-phenyl)-2(R)-hydroxy-ethylamino)-propyl)-1H-indole-2-carboxylic acid, potassium salt, 1-(3-carboxy-benzyl)-5-(2(R,S)-(2(S)-hydroxy-3-phenoxy-propylamino)-propyl)-1H-indole-2-carboxylic acid, potassium salt, 1-(4-carboxy-benzyl)-5-(2(R)-(2-(3-chloro-phenyl)-2(R)-hydroxy-ethylamino)-propyl)-1H-indole-2-carboxylic acid, potassium salt, 1-(3-carbamoyl-benzyl)-5-(2(R, S)-(2-(3-chloro-phenyl)-2(R)-hydroxy-ethylamino)-propyl)-1H-indole-2-carboxylic acid, potassium salt, 1-(3-carbamoyl-benzy)-5-(2(R,S)-(2(S)-hydroxy-3-phenoxy-propylamino)-propyl)-1H-indole-2-carboxylic acid ethyl ester, hydrochloride salt, 1-(3-carbamoyl-benzyl)-5-(2-(R,S) (2(S)-hydroxy-3-phenoxy-propylamino)-propyl)-1H-indole-2-carboxylic acid, potassium salt, 5-(2(R,S)-(2-(3-chloro-phenyl)-2(R)-hydroxy-ethylamino)-propyl)-1-(3-(dimethoxy-phosphoryl)-benzyl)-1H-indole-2-carboxylic acid ethyl ester, hydrochloride salt, 5-(2(R,S)-(2-(3chloro-phenyl)-2(R)-hydroxy-ethylamino)-propyl)-1-(3-(dimethoxy-phosphoryl)-benzyl)-1H-indole-2-carboxylic acid, 5-(2(R,S)-(2-(3-chloro-phenyl)-2(R)-hydroxy-ethylamino)-propyl)-1-(3-phosphono-benzyl)-benzyl)-1H-indole-2-carboxylic acid, hydrobromide salt, 5-(2(R,S)-(2-(3-chloro-phenyl)-2(R)-hydroxy-ethylamino)-propyl)-1-(4-(dimethoxy-phosphoryl)-benzyl)-1H-indole-2-carboxylic acid ethyl ester, hydrochloride salt, 5-(2(R,S)-(2-(3-chloro-phenyl)-2(R)-hydroxy-ethylamino)-propyl)-1-(4-(dimethoxy-phosphoryl)-benzyl)-1H-indole-2-carboxylic acid, 5-(2(R,S)-(2-(3-chloro-phenyl)-2(R)-hydroxy-ethylamino)-propyl)-1-(4-phosphono-benzyl)-benzyl)-1H-indole-2-carboxylic acid, 1-(3-dimethoxy-phosphoryl)-benzyl)-5-(2(R,S)-(2(S)-hydroxy-3-phenoxy-propylamino)-propyl)-1H-indole-2-carboxylic acid ethyl ester, hydrochloride salt, 1-(3-dimethoxy-phosphoryl)-benzyl)-5-(2(R,S)-(2(S)-hydroxy-3-phenoxy-propylamino)-propyl)-1H-indole-2-carboxylic acid, 5-(2(R, S)-(2(S)-hydroxy-3-phenoxy-propylamino)-propyl)-1-(3-phosphono-benzyl)-1H-indole-2-carboxylic acid, 1-(4-dimethoxy-phosphoryl)-benzyl)-5-(2(R,S)-(2(S)-hydroxy-3-phenoxy-propylamino)-propyl)-1H-indole-2-carboxylic acid ethyl ester, hydrochloride salt, 1-(4-dimethoxy-phosphoryl)-benzyl)-5-(2(R,S)-(2(S)-hydroxy-3-phenoxy-propylamino)-propyl)-1H-indole-2-carboxylic acid, 5-(2(R,S)-(2(S)-hydroxy-3-phenoxy-propylamino)-propyl)-1-(4-phosphono-benzyl)-1H-indole-2-carboxylic acid, hydrobromide salt, 5-(2(R,S)-(2-(3-chloro-phenyl)-2(R)-hydroxy-ethylamino)-propyl)-1-(3-dimethylcarbamoyl-benzyl)-1H-indole-2-carboxylic acid ethyl ester, hydrochloride salt, 5-(2(R,S)-(2-(3-chloro-phenyl)-2(R)-hydroxy-ethylamino)-propyl)-1-(3-dimethylcarbamoyl-benzyl)-1H-indole-2-carboxylic acid, potassium salt, 1-(4-dimethylcarbamoyl-benzyl)-5-(2(R,S)-(2(S)-hydroxy-3-phenoxy-propylamino)-propyl)-1H-indole-2-carboxylic acid, 5-(2(R)-(2-(3-chloro-phenyl)-2(R)-hydroxy-ethylamino)-propyl)-1-pyridin-4-ylmethyl-1H-indole-2-carboxylic acid methyl ester, hydrochloride salt, 5-(2(R)-(2-(3-chloro-phenyl)-2(R)-hydroxy-ethylamino)-propyl)-1 -pyridin-4-ylmethyl-1H-indole-2-carboxylic acid, potassium salt, 5-(2(R,S)-(2-(3-chloro-phenyl)-2(R)-hydroxy-ethylamino)-propyl)-1-pyrimidin4-ylmethyl-1H-indole-2-carboxylic acid, 5-(2(R,S)-(2-(3-chloro-phenyl)-2(R)-hydroxy-ethylamino)-propyl)-1-(4-methanesulfonyl-benzyl)-1H-indole-2-carboxylic acid methyl ester, hydrochloride salt, 5-(2(R,S)-(2-(3-chloro-phenyl)-2(R)-hydroxy-ethylamino)-propyl)-1-(4-methanesulfonyl-benzyl)-1H-indole-2-carboxylic acid, 1-benzyl-(5-(2 (R,S)-(2-(3-chloro-phenyl)-2(R)-hydroxy-ethylamino)-propyl)-1H-indol-2-yl)-acetic acid methyl ester, hydrochloride salt, 1-benzyl-(5-(2(R,S)-(2-(3-chloro-phenyl)-2(R)-hydroxy-ethylamino)-propyl)-1H-indol-2-yl)-acetic acid, 1-benzyl-(5-(2(R,S)-(2(S)-hydroxy-3-phenoxy-propylamino)-propyl)-1H-indol-2-yl)-acetic acid methyl ester, hydrochloride salt, 1-benzyl-(5-(2(R,S)-(2(S)-hydroxy-3-phenoxy-propylamino)-propyl)-1H-indol-2-yl)-acetic acid, 1-[2-(2-[1,2,4]oxadiazol-3-yl-benzo [b]thiophen-5-yloxy)-ethylamino]-3-phenoxy-propan-2(S)-ol, 5-[2-(2(S)-hydroxy-3-phenoxy-propylamino)-ethoxy]-benzo[b]thiophene-2-carboxylic acid, 5-[2-(2(S)-hydroxy-3-phenoxy-propylamino)-ethoxy]-benzo[b]thiophene-2-carboxylic acid ethyl ester, 1-[2-(2-[1,2,4]oxadiazol-3-yl-benzothiazol-6-yloxy)-ethylamino]-3-phenoxy-propan-2(S)-ol, 1-phenoxy-3-{2-[2-(1H-tetrazol-5-yl)-benzothiazol-6-yloxy]-ethylamino}-propan-2(S)-ol, 1-benzyl-5-(2(R,S)-(2(R,S)-hydroxy-2-tetrazolo(1,5-a)pyridine-6-yl-ethylamino)-propyl)-1H-indole-2-carboxylic acid ethyl ester dihydrochloride salt, 1-benzyl-5-(2(R,S)-(2(R,S)-hydroxy-2-tetrazolo(1,5-a)pyridine-6-yl-ethylamino)-propyl)-1H-indole-2-carboxylic acid, 5-(2(R,S)-(2(R)-hydroxy-3-phenoxy-propylamino)-propyl)-1-(2-methanesulfonylamino-benzyl)-1H-indole-2-carboxylic acid.

Other compounds of formula I are:

1-benzyl-5-(2(R)-(2-(3-chloro-phenyl)-2(R)-hydroxy-ethylamino)-propyl)-1H-indole-2-carboxylic acid, 1-benzyl-5-(2-((2S)-hydroxy-3-phenoxy-propylamino)-1H-indole-2-carboxylic acid, 5-(2-((2S)-hydroxy-3-phenoxy-propylamino)-propyl)-1H-indole-2-carboxylic acid, (5-((2-(R)-(2-(3-chloro-phenyl)-(2R)-hydroxy-ethylamino)-propyl)-benzofuran-2-yl)-acetic acid, 5-(2-(R)-(2-(3-chloro-phenyl)-2(R)-hydroxy-ethylamino)-propyl)-indol-2-carboxylic acid, 1-methyl-5-(2-(R)-(2-(3-chloro-phenyl)-2(R)-hydroxy-ethylamino)-propyl)-indol-2-carboxylic acid, 5-(2-(R)-(2-(3-chloro-phenyi)-2(R)-hydroxy-ethylamino)-propyl)-benzofuran-2-carboxylic acid, methyl-5-(2-(R)-(2-(3-chloro-phenyl)-2(R)-hydroxy-ethylamino)-propyl)-benzofuran-2-carboxylic acid, 5-(2-(2-(3-chloro-phenyl)-2-hydroxy-ethylamino)-propyl)-1-H-indole-2-carboxylic acid, 5-(2-(2-(3-chloro-phenyl)-2-hydroxy-ethylamino)-propyl)-1-H-indole-2-carboxylic acid methyl ester, 1-benzyl-5-(2-(2-(3-chloro-phenyl)-2-hydroxy-ethylamino)-propyl)-1-H-indole-2-carboxylic acid, 1-benzyl-5-(2-(2-(3-chloro-phenyl)-2-hydroxy-ethylamino)-propyl)-1-H-indole-2-carboxylic acid methyl ester, 5-(2-(2-(3-chloro-phenyl)-2-hydroxy-ethylamino)-propyl)-1-phenyl-1-H-indole-2-carboxylic acid, 5-(2-(2-(3-chloro-phenyl)-2-hydroxy-ethylamino)-propyl)-1-ethyl-1-H-indole-2-carboxylic acid, 5-(2-(2-(3-chloro-phenyl)-2-hydroxy-ethylamino)-propyl)-1-ethyl-1-H-indole-2-carboxylic acid methyl ester, 5-(2-(2-(3-chloro-phenyl)-2-hydroxy-ethylamino)-propyl)-1-methyl-1-H-indole-2-carboxylic acid, 5-(2-(2-(3-chloro-phenyl)-2-hydroxy-ethylamino)-propyl)-1-methyl-1H-indole-2-carboxylic acid methyl ester, 5-(2-(2-(3-chloro-phenyl)-2-hydroxy-ethylamino)-propyl)-1-(2-hydroxyethyl)-1H-indole-2-carboxylic acid, 5-(2-(2-(3-chloro-phenyl)-2-hydroxy-ethylamino)-propyl)-1-methanesulfonylmethyl-1H-indole-2-carboxylic acid, 5-(2-(2-(3-chloro-phenyl)-2-hydroxy-ethylamino)-propyl)-1-cyclohexylmethyl-1H-indole-2-carboxylic acid, 5-(2-(2-(3-chloro-phenyl)-2-hydroxy-ethylamino)-propyl)-1-(4-pyridylmethyl)-1H-indole-2-carboxylic acid, 5-(2-(2-(3-chloro-phenyl)-2-hydroxy-ethylamino)-propyl)-1-(4-pyridylmethyl)-1H-indole-2-carboxylic acid methyl ester, 5-(2-(2-(3-chloro-phenyl)-2-hydroxy-ethylamino)-propyl)-1-(3-pyridylmethyl)-1H-indole-2-carboxylic acid, 5-(2-(2-(3-chloro-phenyl)-2-hydroxy-ethylamino)-propyl)-1-(3-pyridylmethyl)-1H-indole-2-carboxylic acid methyl ester, 5-(2-(2-(3-chloro-phenyl)-2-hydroxy-ethylamino)-propyl)-1-(2-pyridylmethyl)-1H-indole-2-carboxylic acid, 5-(2-(2-(3-chloro-phenyl)-2-hydroxy-ethylamino)-propyl)-1-(2-pyridylmethyl)-1H-indole-2-carboxylic acid methyl ester, 5-(2-(2-(3-chloro-phenyl)-2-hydroxy-ethylamino)-propyl)-1-pyrizinylmethyl-1H-indole-2-carboxylic acid, 5-(2-(2-(3-chloro-phenyl)-2-hydroxy-ethylamino)-propyl)-1-(2-methylthiazol4-yl-methyl)-1H-indole-2-carboxylic acid, 5-(2-(2-(3-chloro-phenyl)-2-hydroxy-ethylamino)-propyl)-1-(5-methyl-1,2,4-oxadiazol-3-yl-methyl-1H-indole-2-carboxylic acid, 5-(2-(2-(3-chloro-phenyl)-2-hydroxy-ethylamino)-propyl)-1-(2-pyrimidinylmethyl)-1H-indole-2-carboxylic acid, 5-(2-(2-(3-chloro-phenyl)-2-hydroxy-ethylamino)-propyl)-1-(2-pyrimidinylmethyl)-1H-indole-2-carboxylic acid methyl ester, 5-(2-(2-(3-chloro-phenyl)-2-hydroxy-ethylamino)-propyl)-1-(4-pyrimidinylmethyl)-1H-indole-2-carboxylic acid, 5-(2-(2-(3-chloro-phenyl)-2-hydroxy-ethylamino)-propyl)-1-(4-pyrimidinylmethyl)-1H-indole-2-carboxylic acid methyl ester, 5-(2-(2-(3-chloro-phenyl)-2-hydroxy-ethylamino)-propyl)-1-(5-pyrimidinylmethyl)-1H-indole-2-carboxylic acid, 5(2-(2-(3-chloro-phenyl)-2-hydroxy-ethylamino)-propyl)-1-(5-pyrimidinylmethyl)-1H-indole-2-carboxylic acid methyl ester, 5-(2-(2-(3-chloro-phenyl)-2-hydroxy-ethylamino)-propyl)-1-(4-(methylsulfonyl)phenylmethyl)-1H-indole-2-carboxylic acid, 5-(2-(2-(3-chloro-phenyl)-2-hydroxy-ethylamino)-propyl)-1-((2-carboxyphenyl)methyl)-1H-indole-2-carboxylic acid, 5-(2-(2-(3-chloro-phenyl)-2-hydroxy-ethylamino)-propyl)-1-(((2-carboxymethyl)phenyl)methyl)-1H-indole-2-carboxylic acid methyl ester, 5-(2-(2-(3-chloro-phenyl)-2-hydroxy-ethylamino)-propyl)-1-((3-carboxyphenyl)methyl)-1H-indole-2-carboxylic acid, 5-(2-(2-(3-chloro-phenyl)-2-hydroxy-ethylamino)-propyl)-1-(((3-carboxymethyl)phenyl)methyl)-1H-indole-2-carboxylic acid methyl ester, 5-(2-(2-(3-chloro-phenyl)-2-hydroxy-ethylamino)-propyl)-1-((4-carboxyphenyl)methyl)-1H-indole-2-carboxylic acid, 5-(2-(2-(3-chloro-phenyl)-2-hydroxy-ethylamino)-propyl)-1-(((4-carboxymethyl)phenyl)methyl)-1H-indole-2-carboxylic acid methyl ester, 5-(2-(2-(3-chloro-phenyl)-2-hydroxy-ethylamino)-propyl)-1-(1-imidazolylmethyl)-1H-indole-2-carboxylic acid, 5-(2-(2-(3-chloro-phenyl)-2-hydroxy-ethylamino)-propyl)-1-(1-imidazolylmethyl)-1H-indole-2-carboxylic acid methyl ester, 5-(2-(2-(3-chloro-phenyl)-2-hydroxy-ethylamino)-propyl)-1-(1,2,4-triazol-4-yl-methyl)-1H-indole-2-carboxylic acid, 5-(2-(2-(3-chloro-phenyl)-2-hydroxy-ethylamino)-propyl)-1-(1,2,4-triazol-4-yl-methyl)-1H-indole-2-carboxylic acid methyl ester, 1-benzyl-(5-(2-(2-(3-chloro-phenyl)-2-hydroxy-ethylamino)-propyl)-1H-indol-2-yl)-acetic acid, 1-benzyl-(5-(2-(2-(3-chloro-phenyl)-2-hydroxy-ethylamino)-propyl)-1H-indol-2-yl)-acetic acid methyl ester, (5-(2-(2-(3-chloro-phenyl)-2-hydroxy-ethylamino)-propyl)-1H-indol-2-yl)-acetic acid, (5-(2-(2-(3-chloro-phenyl)-2-hydroxy-ethylamino)-propyl)-1H-indol-2-yl)-acetic acid methyl ester, 5-[2-[2-[3-chlorophenyl]-2-hydroxy-ethylamino]-propyl]-1-[4-[methanesulfonyl-methyl-amino]-benzyl]-1H-indole-2-carboxylic acid, 5-[2-[2-[3-bromophenyl]-2-hydroxy-ethylamino]-propyl]-1-[4-[methanesulfonyl-methyl-amino]-benzyl]-1H-indole-2-carboxylic acid, 5-[2-[2-[3-(trifluoromethyl)phenyl]-2-hydroxy-ethylamino]-propyl]-1-[4-[methanesulfonyl-methyl-amino]-benzyl]-1H-indole-2-carboxylic acid, 5-[2-[2-phenyl-2-hydroxy-ethylamino]-propyl]-1-[4-[methanesulfonyl-methyl-amino]-benzyl]-1H-indole-2-carboxylic acid, 5-[2-[2-[6-aminopyridin-3-yl]-2-hydroxy-ethylamino]-propyl]-1-[4-[methanesulfonyl-methyl-amino]-benzyl]-1H-indole-2-carboxylic acid, 5-[2-[2-[6-amino-5-chloropyridin-3-yl]-2-hydroxy-ethylamino]-propyl]-1-[4-[methanesulfonyl-methyl-amino]-benzyl]-1H-indole-2-carboxylic acid, 5-[2-[2-[6-amino-5-cyanopyridin-3-yl]-2-hydroxy-ethylamino]-propyl]-1-[4-[methanesulfonyl-methyl-amino]-benzyl]-1H-indole-2-carboxylic acid, 5-[2-[2-[6-aminopyrimidin-3-yl]-2-hydroxy-ethylamino]-propyl]-1-[4-[methanesulfonyl-methyl-amino]-benzyl]-1H-indole-2-carboxylic acid, 5-[2-[2-hydroxy-3-phenoxy-propylamino]-propyl-1-[4-[methanesulfonyl-methyl-amino]-benzyl]-1H-indole-2-carboxylic acid, 5-[2-[2-[3-chlorophenyl]-2-hydroxy-ethylamino]-propyl]-1-[3-[methanesulfonyl-ethyl-amino]-benzyl]-1H-indole-2-carboxylic acid, 5-[2-[2-[3-bromophenyl]-2-hydroxy-ethylamino]-propyl]-1-[3-[methanesulfonyl-methyl-amino]-benzyl]-1H-indole-2-carboxylic acid, 5-[2-[2-[3-(trifluoromethyl)phenyl]-2-hydroxy-ethylamino]-propyl]-1-[3-[methanesulfonyl-methyl-amino]-benzyl]-1H-indole-2-carboxylic acid, 5-[2-[2-phenyl-2-hydroxy-ethylamino]-propyl]-1-[3-[methanesulfonyl-methyl-amino]-benzyl]-1H-indole-2-carboxylic acid, 5-[2-[2-[6-aminopyridin-3-yl]-2-hydroxy-ethylamino]-propyl]-1-[3-[methanesulfonyl-methyl-amino]-benzyl]-1H-indole-2-carboxylic acid, 5-[2-[2-[6-amino-5-chloropyridin-3-yl]-2-hydroxy-ethylamino]-propyl]-1-[3-[methanesulfonyl-methyl-amino]-benzyl]-1H-indole-2-carboxylic acid, 5-[2-[2-[6-amino-5-cyanopyridin-3-yl]-2-hydroxy-ethylamino]-propyl]-1-[3-[methanesulfonyl-methyl-amino]-benzyl]-1H-indole-2-carboxylic acid, 5-[2-[2-[6-aminopyrimidin-3-yl]-2-hydroxy-ethylamino]-propyl]-1-[3-[methanesulfonyl-methyl-amino]-benzyl]-1H-indole-2-carboxylic acid, 5-[2-[2-hydroxy-3-phenoxy-propylamino]-propyl-1-[3-[methanesulfonyl-methyl-amino]-benzyl]-1H-indole-2-carboxylic acid, 5-[2-[2-[3-chlorophenyl]-2-hydroxy-ethylamino]-propyl]-1-[3-[methanesulfonylamino]-benzyl]-1H-indole-2-carboxylic acid, 5-[2-[2-[3-bromophenyl]-2-hydroxy-ethylamino]-propyl]-1-[3-[methanesulfonylamino]-benzyl]-1H-indole-2-carboxylic acid, 5-[2-[2-[3-(trifluoromethyl)phenyl]-2-hydroxy-ethylamino]-propyl]-1-[3-[methanesulfonylamino]-benzyl]-1H-indole-2-carboxylic acid, 5-[2-[2-phenyl-2-hydroxy-ethylamino]-propyl]-1-[3-[methanesulfonylamino]-benzyl]-1H-indole-2-carboxylic acid, 5-[2-[2-[6-aminopyridin-3-yl]-2-hydroxy-ethylamino]-propyl]-1-[3-[methanesulfonylamino]-benzyl]-1H-indole-2-carboxylic acid, 5-[2-[2-[6-amino-5-chloropyridin-3-yl]-2-hydroxy-ethylamino]-propyl]-1-[3-[methanesulfonylamino]-benzyl]-1H-indole-2-carboxylic acid, 5-[2-[2-[6-amino-5-cyanopyridin-3-yl]-2-hydroxy-ethylamino]-propyl]-1-[3-[methanesulfonylamino]-benzyl]-1H-indole-2-carboxylic acid, 5-[2-[2-[6-aminopyrimidin-3-yl]-2-hydroxy-ethylamino]-propyl]-1-[3-[methanesulfonylamino]-benzyl]-1H-indole-2-carboxylic acid, 5-[2-[2-hydroxy-3-phenoxy-propylamino]-propyl-1-[3-[methanesulfonylamino]-benzyl]-1H-indole-2-carboxylic acid, 5-[2-[2-[3-bromophenyl]-2-hydroxy-ethylamino]-propyl]-1-[4-[methanesulfonylamino]-benzyl]-1H-indole-2-carboxylic acid, 5-[2-[2-[3-(trifluoromethyl)phenyl]-2-hydroxy-ethylamino]-propyl]-1-[4-[methanesulfonyamino]-benzyl]-1H-indole-2-carboxylic acid, 5-[2-[2-phenyl-2-hydroxy-ethylamino]-propyl]-1-[4-[methanesulfonylamino]-benzyl]-1H-indole-2-carboxylic acid, 5-[2-[2-[6-aminopyridin-3-yl]-2:hydroxy-ethylamino]3-propyl]-1-[4-[methanesulfonylamino]-benzyl]-1H-indole-2-carboxylic acid, 5-[2-[2-[6-amino-5-chloropyridin-3-yl -2-hydroxy-ethylamino]-propyl]-1-[4-[methanesulfonylamino]-benzyl]-1H-indole-2-carboxylic acid, 5-[2-[2-[6-amino-5-cyanopyridin-3-yl]-2-hydroxy-ethylamino]-propyl]-1-[4-[methanesulfonylamino]-benzyl]-1H-indole-2-carboxylic acid, 5-[2-[2-[6-aminopyrimidin-3-yl]-2-hydroxy-ethylamino]-propyl]-1-[4-[methanesulfonylamino]-benzyl]-1H-indole-2-carboxylic acid, 5-[2-[2-[3-chlorophenyl]-2-hydroxy-ethylamino]-propy]-1-[3-[trifluoromethanesulfonylamino]-benzyl]-1H-indole-2-carboxylic acid, 5-[2-[2-[3-bromophenyl]-2-hydroxy-ethylamino]-propyl]-1-(3-[trifluoromethanesulfonylamino]-benzyl]-1H-indole-2-carboxylic acid, 5-[2-[2-[3-(trifluoromethyl)phenyl]-2-hydroxy-ethylamino]-propyl]-1-[3-[trifluoromethanesulfonylamino]-benzyl]-1H-indole-2-carboxylic acid, 5-[2-[2-phenyl-2-hydroxy-ethylamino]-propyl]-1-[3-[trifluoromethanesulfonylamino]-benzyl]-1H-indole-2-carboxylic acid, 5-[2-[2-[6-aminopyridin-3-yl]-2-hydroxy-ethylamino]-propyl]-1-[3-[trifluoromethanesulfonylamino]-benzyl]-1H-indole-2-carboxylic acid, 5-[2-[2-[6-amino-5-chloropyridin-3-yl]-2-hydroxy-ethylamino]-propyl]-1-[3-[trifluoromethanesulfonylamino]-benzyl]-1H-indole-2-carboxylic acid, 5-[2-[2-[6-amino-5-cyanopyridin-3-yl]-2-hydroxy-ethylamino]-propyl]-1-[3-[trifluoromethanesulfonylamino]-benzyl]-1H-indole-2-carboxylic acid, 5-[2-[2-[6-aminopyrimidin-3-yl]-2-hydroxy-ethylamino]-propyl]-1-[3-[trifluoromethanesulfonylamino]-benzyl]-1H-indole-2-carboxylic acid, 5-[2-[2-hydroxy-3-phenoxy-propylaminol-propyl-1-[3-[trifluoromethanesulfonyl-amino]-benzyl]-1H-indole-2-carboxylic acid, 5-[2-[2-[3-chlorophenyl]-2-hydroxy-ethylamino]-propy]-1-[4-[trifluoromethanesulfonylaminol-benzyl]-1H-indole-2-carboxylic acid, 5-[2-[2-[3-bromophenyl]-2-hydroxy-ethylamino]-propyl]-1-[4-[trifluoromethanesulfonylamino]-benzyl -1H-indole-2-carboxylic acid, 5-[2-[2-[3-(trifluoromethyl)phenyl]-2-hydroxy-ethylamino]-propyl]-1-[4-[trifluoromethanesulfonylamino]-benzyl]-1H-indole-2-carboxylic acid, 5-[2-[2-phenyl-2-hydroxy-ethylamino]-propyl]-1-[4-[trifluoromethanesulfonylamino]-benzyl]-1H-indole-2-carboxylic acid, 5-[2-[2-[6-aminopyridin-3-yl]-2-hydroxy-ethylamino]-propyl]-1-[4-[trifluoromethanesulfonylamino]-benzyl]-1H-indole-2-carboxylic acid, 5-[2-[2-[6-amino-5-chloropyridin-3-yl]-2-hydroxy-ethylamino]-propyl]-1-[4-[trifluoromethanesulfonylamino]-benzyl]-1H-indole-2-carboxylic acid, 5-[2-[2-[6-amino-5-cyanopyridin-3-yl]-2-hydroxy-ethylamino]-propyl]-1-[4-[trifluoromethanesulfonylamino]-benzyl]-1H-indole-2-carboxylic acid, 5-[2-[2-[6-aminopyrimidin-3-yl]-2-hydroxy-ethylamino]-propyl]-1-[4-[trifluoromethanesulfonylamino]-benzyl]-1H-indole-2-carboxylic acid, 5-[2-[2-hydroxy-3-phenoxy-propylamino]-propyl-1-[4-[trifluoromethanesulfonyl-amino]-benzyl]-1H-indole-2-carboxylic acid, 5-[2-[2-[3-chlorophenyl]-2-hydroxy-ethylamino]-propyl]1-1-[3-[trifluoromethanesulfonyl-methyl-amino]-benzyl]-1H-indole-2-carboxylic acid, 5-[2-[2-[3-bromophenyl]-2-hydroxy-ethylamino]-propyl]-1-[3-[trifluoromethanesulfonyl-methyl-amino]-benzyl]-1H-indole-2-carboxylic acid, 5-[2-[2-[3-(trifluoromethyl)phenyl]-2-hydroxy-ethylamino]-propyl]-1-[3-[trifluoromethanesulfonyl-methy]-aminol-benzyl]-1H-indole-2-carboxylic acid, 5-[2-[2-phenyl-2-hydroxy-ethylamino]-propyl]-1 -[3-[trifluoromethanesulfonyl-methyl-amino]-benzyl]-1H-indole-2-carboxylic acid, 5-[2-[2-6-aminopyridin-3-yl]-2-hydroxy-ethylamino]-propyl]-1-[3-[trifluoromethanesulfonyl-methyl-amino]-benzyl]-1H-indole-2-carboxylic acid, 5-[2-[2-[6-amino-5-chloropyridin-3-yl]-2-hydroxy-ethylamino]-propyl]-1-[3-[trifluoromethanesulfonyl-methyl-amino]-benzyl]-1H-indole-2-carboxylic acid, 5-[2-[2-[6-amino-5-cyanopyridin-3-yl]-2-hydroxy-ethylamino]-propyl]-[3-[trifluoromethanesulfonyl-methyl-amino]-benzyl]-1H-indole-2-carboxylic acid, 5-[2-[2-[6-aminopyrimidin-3-yl]-2-hydroxy-ethylamino]-propyl]-1-[3-[trifluoromethanesulfonyt-methyl-aminol-benzyl]-1H-indole-2-carboxylic acid, 5-[2-[2-hydroxy-3-phenoxy-propylaminol-propyl-1-[3-[trifluoromethanesulfonyl-methyl-amino]-benzyl]-1H-indole-2-carboxylic acid, 5-[2-[2-[3-chlorophenyl]-2-hydroxy-ethylamino]-propyl]-1-[4-[trifluoromethanesulfonyl-methyl-amino]-benzyl]-1H-indole-2-carboxylic acid, 5-[2-[2-[3-bromophenyl]-2-hydroxy-ethylamino]-propyl]-1-[4-[trifluoromethanesulfonyl-methyl-amino]-benzyl]-1H-indole-2-carboxylic acid, 5-[2-[2-[3-(trifluoromethyl)phenyl]-2-hydroxy-ethylamino]-propyl]-1-[4-[trifluoromethanesulfonyl-methyl-amino]-benzyl]-1H-indole-2-carboxylic acid, 5-[2-[2-phenyl-2-hydroxy-ethylamino]-propyl]-1-[4-[trifluoromethanesulfonyl-methyl-amino]-benzyl]-1H-indole-2-carboxylic acid, 5-[2-[2-[6-aminopyridin-3-yl]-2-hydroxy-ethylamino]-propyl]-1-[4-[trifluoromethanesulfonyl-methyl-amino]-benzyl]-1H-indole-2-carboxylic acid, 5-[2-[2-[6-amino-5-chloropyridin-3-yl]-2-hydroxy-ethylamino]-propyl]-1-[4-[trifluoromethanesulfonyl-methyl-amino]-benzyl]-1H-indole-2-carboxylic acid, 5-[2-[2-[6-amino-5-cyanopyridin-3-yl]-2-hydroxy-ethylamino]-propyl]-1-[4-[trifluoromethanesulfonyl-methyl-amino]-benzyl]-1H-indole-2-carboxylic acid, 5-[2-[2-[6-aminopyrimidin-3-yl]-2-hydroxy-ethylamino]-propyl]-1-[4-[trifluoromethanesulfonyl-methyl-amino]-benzyl]-1H-indole-2-carboxylic acid, 5-[2-[2-hydroxy-3-phenoxy-propylamino]-propyl-1-[4-[trifluoromethanesulfonyl-methyl-amino]-benzyl]-1H-indole-2-carboxylic acid, 5-[2-[2-[3-chlorophenyl]-2-hydroxy-ethylamino]-propyl]-1-[4-[2,2,2-trifluoroethanesulfonyl-methyl-amino]-benzyl]-1H-indole-2-carboxylic acid, 5-[2-[2-[3-bromophenyl]-2-hydroxy-ethylamino]-propyl]-1-[4-[2,2,2-trifluoroethanesulfonyl-methyl-amino]-benzyl]-1H-indole-2-carboxylic acid, 5-[2-[2-[3-(trifluoromethyl)phenyl]-2-hydroxy-ethylamino]-propyl]-1-[4-[2,2,2-trifluoroethanesulfonyl-methyl-amino]-benzyl]-1H-indole-2-carboxylic acid, 5-[2-[2-phenyl-2-hydroxy-ethylamino]-propyl]-1-[4-[2,2,2-trifluoroethanesulfonyl-methyl-amino]-benzyl]-1H-indole-2-carboxylic acid, 5-[2-[2-[6-aminopyridin-3-yl]-2-hydroxy-ethylamino]-propyl]-1-[4-[2,2,2-trifluoroethanesulfonyl-methyl-amino]-benzyl]-1H-indole-2-carboxylic acid, 5-[2-[2-[6-amino-5-chloropyridin-3-yl]-2-hydroxy-ethylamino]-propyl]-1-trifluoroethanesulfonyl-methyl-amino]-benzyl]-1H-indole-2-carboxylic acid, 5-[2-[2-[6-amino-5-cyanopyridin-3-yl]-2-hydroxy-ethylamino]-propyl]-1-[4-[2,2,2-trifluoroethanesulfonyl-methyl-amino]-benzyl]-1H-indole-2-carboxylic acid, 5-[2-[2-[6-aminopyrimidin-3-yl]-2-hydroxy-ethylamino]-propyl]-1-[4-[2,2,2-trifluoroethanesulfonyl-methyl-amino]-benzyl]-1H-indole-2-carboxylic acid, 5-2-t2-hydroxy-3-phenoxy-propylamino]-propyl-1-[4-[-2,2,2-trifluoroethanesulfonyl-methyl-amino]-benzyl]-1H-indole-2-carboxylic acid, 5-[2-[2-[3-chlorophenyl]-2-hydroxy-ethylamino]-propyl]-1-[3-[2,2,2-trifluoroethanesulfonyl-methyl-amino]-benzyl]-1H-indole-2-carboxylic acid, 5-[2-[2-[3-bromophenyl]-2-hydroxy-ethylamino]-propyl]-1-[3-[2,2,2-trifluoroethanesulfonyl-methyl-amino]-benzyl]-1H-indole-2-carboxylic acid, 5-[2-[2-[3-(trifluoromethyl)phenyl]-2-hydroxy-ethylamino]-propyl]-1-[3-[2,2,2-trifluoroethanesulfonyl-methyl-amino]-benzyl]-1H-indole-2-carboxylic acid, 5-[2-[2-phenyl-2-hydroxy-ethylamino]-propyl]-1-[3-[2,2,2-trifluoroethanesulfonyl-methyl-amino]-benzyl]-1H-indole-2-carboxylic acid, 5-[2-[2-[6-aminopyridin-3-yl]-2-hydroxy-ethylamino]-propyl]-1-[3-[2,2,2-trifluoroethanesulfonyl-methyl-amino]-benzyl]-1H-indole-2-carboxylic acid, 5-[2-[2-[6amino-5-chloropyridin-3-yl]-2-hydroxy-ethylamino]-propyl]-1-[3-trifluoroethanesulfonyl-methyl-amino]-benzyl]-1H-indole-2-carboxylic acid, 5-[2-[2-[6-amino-5-cyanopyridin-3-yl]-2-hydroxy-ethylamino]-propyl]-1-[3-[2,2,2-trifluoroethanesulfonyl-methyl-amino]-benzyl]-1H-indole-2-carboxylic acid, 5-[2-[2-[6-aminopyrimidin-3-yl]-2-hydroxy-ethylamino]-propyl]-1-[3-[2,2,2-trifluoroethanesulfonyl-methyl-amino]-benzyl]-1H-indole-2-carboxylic acid, 5-[2-[2-hydroxy-3-phenoxy-propylamino]-propyl-1-[3-[2,2,2-trifluoroethanesulfonyl-methyl-amino]-benzyl]-1H-indole-2-carboxylic acid, 5-[2-[2-[3-chlorophenyl]-2-hydroxy-ethylamino]-propyl]-1-[3-sulfamoyl-benzyl]-1H-indole-2-carboxylic acid, 5-[2-[2-[3-bromophenyl]-2-hydroxy-ethylamino]-propyl]-1-[3-sulfamoyl-benzyl]-1H-indole-2-carboxylic acid, 5-[2-[2-[3-(trifluoromethyl)phenyl]-2-hydroxy-ethylamino]-propyl]-1-[3-sulfamoyl-benzyl]-1H-indole-2-carboxylic acid, 5-[2-[2-phenyl-2-hydroxy-ethylamino]-propyl]-1-[3-sulfamoyl-benzyl]-1H-indole-2-carboxylic acid, 5-[2-[2-[6-aminopyridin-3-yl]-2-hydroxy-ethylamino]-propyl]-1-[3-sulfamoyl-benzyl]-1H-indole-2-carboxylic acid, 5-[2-[2-[6-amino-5-chloropyridin-3-yl]-2-hydroxy-ethylamino]-propyl]-[3-sulfamoyl-benzyl-]-1H-indole-2-carboxylic acid, 5-[2-[2-[6-amino-5-cyanopyridin-3-yl]-2-hydroxy-ethylamino]-propyl]-1-[3-sulfamoyl-benzyl]-1H-indole-2-carboxylic acid, 5-[2-[2-[6-aminopyrimidin-3-yl]-2-hydroxy-ethylamino]-propyl]-1-[3-sulfamoyl-benzyl]-1H-indole-2-carboxylic acid, 5-[2-[2-hydroxy-3-phenoxy-propylamino]-propyl-1-[3-sulfamoyl-benzyl]-1H-indole-2-carboxylic acid, 5-[2-[2-[3-chlorophenyl]-2-hydroxy-ethylamino]-propyl]-1-[4-sulfamoyl-benzyl]-1H-indole-2-carboxylic acid, 5-[2-[2-[3-bromophenyl]-2-hydroxy-ethylamino]-propyl]-1-[4-sulfamoyl-benzyl]-1H-indole-2-carboxylic acid, 5-[2-[2-[3-(trifluoromethyl)phenyl]-2-hydroxy-ethylamino]-propyl]-1-[4-sulfamoyl-benzyl]-1H-indole-2-carboxylic acid, 5-[2-[2-phenyl-2-hydroxy-ethylamino]-propyl]-1-[4-sulfamoyl-benzyl]-1H-indole-2-carboxylic acid, 5-[2-[2-[6-aminopyridin-3-yl]-2-hydroxy-ethylamino]-propyl]-1-[4-sulfamoyl-benzyl]-1H-indole-2-carboxylic acid, 5-[2-[2-[6-amino-chloropyridin-3-yl]-2-hydroxy-ethylamino]-propyl]-1-[4-sulfamoyl-benzyl]-1H-indole-2-carboxylic acid, 5-[2-[2-[6-amino-5-cyanopyridin-3-yl]-2-hydroxy-ethylamino]-propyl]-1-[4sulfamoyl-benzyl]-1H-indole-2-carboxylic acid, 5-[2-[2-[6-aminopyrimidin-3-yl]-2-hydroxy-ethylamino]-propyl]-1-[4-sulfamoyl-benzyl]-1H-indole-2-carboxylic acid, 5-[2-[2-hydroxy-3-phenoxy-propylamino]-propyl-1-[4-sulfamoyl-benzyl]-1H-indole-2-carboxylic acid, 5-[2-[2-[3-chlorophenyl]-2-hydroxy-ethylamino]-propyl]-1-[3-methylsulfamoyl-benzyl]-1H-indole-2-carboxytic acid, 5-[2-[2-[3-bromophenyl]-2-hydroxy-ethylamino]-propyl]-1-[3-methylsulfamoyl-benzyl]-1H-indole-2- carboxylic acid, 5-[2-[2-[3-(trifluoromethyl)phenyl]-2-hydroxy-ethylamino]-propyl]-1-[3-methylsulfamoyl-benzyl]-1H-indole-2-carboxylic acid, 5-[2-[2-phenyl-2-hydroxy-ethylamino]-propyl]-1-[3-methylsulfamoyl-benzyl]-1H-indole-2-carboxylic acid, 5-[2-[2-[6-aminopyridin-3-yl]-2-hydroxy-ethylamino]-propyl]-1-[3-methylsulfamoyl-benzyl]-1H-indole-2-carboxylic acid, 5-[2-[2-[6-amino-5-chloropyrid in-3-yl]-2-hydroxy-ethylamino]-propyl]-1-[3-methylsulfamoyl-benzyl]-1H-indole-2-carboxylic acid, 5-[2-[2-[6-amino-5-cyanopyridin-3-yl]-2-hydroxy-ethylamino]-propyl-1-[3-methylsulfamoyl-benzyl]-1H-indole-2-carboxylic acid, 5-[2-[2-[6-aminopyrimidin-3-yl]-2-hydroxy-ethylamino]-propyl]-1-1-[3-methylsulfamoyl-benzyl]-1H-indote-2-carboxylic acid, 5-[2-[2-hydroxy-3-phenoxy-propylamino]-propyl-1-[3-methylsulfamoyl-benzyl]-1H-indole-2-carboxylic acid, 5-[2-[2-[3-chlorophenyl]-2-hydroxy-ethylamino]-propyl]-1-[4-methylsulfamoyl-benzyl]-1H-indole-2-carboxylic acid, 5-[2-[2-[3-bromophenyl]-2-hydroxy-ethylamino]-propyl]-1-[4-methylsulfamoyl-benzyl]-1H-indole-2-carboxylic acid, 5-[2-[2-[3-(trifluoromethyl)phenyl]-2-hydroxy-ethylamino]-propyl]-1-[4-methylsulfamoyl-benzyl]-1H-indole-2-carboxylic acid, 5-[2-[2-phenyl-2-hydroxy-ethylamino]-propyl]-1-[4-methylsulfamoyl-benzyl]-1H-indole-2-carboxylic acid, 5-[2-[2-[6-aminopyridin-3-yl]-2-hydroxy-ethylamino]-propyl]-1-[4-methylsulfamoyl-benzyl]-1H-indole-2-carboxylic acid, 5-[2-[2-[6-amino-5-chloropyridin-3-yl]-2-hydroxy-ethylamino]-propyl]-1-[4-methylsulfamoyl-benzyl]-1H-indole-2-carboxyiic acid, 5-[2-[2-[6-amino-5-cyanopyridin-3-yl]-2-hydroxy-ethylamino]-propyl]-1-[4-methylsulfamoyl-benzyl]-1H-indole-2-carboxylic acid, 5-[2-[2-[6-aminopyrimidin-3-yl]-2-hydroxy-ethylamino]-propyl]-1-[4-methylsulfamoyl-benzyl]-1H-indole-2-carboxylic acid, 5-[2-[2-hydroxy-3-phenoxy-propylamino]-propyl-1-[4-methylsulfamoyl-benzyl]-1H-indole-2-carboxylic acid, 5-[2-[2-[3-chlorophenyl]-2-hydroxy-ethylamino]-propyl]-1-[3-dimethylsulfamoyl-benzyl]-1H-indole-2-carboxylic acid, 5-[2-[2-[3-bromophenyl]-2-hydroxy-ethylamino]-propyl]-1-[3-dimethylsulfamoyl-benzyl]-1H-indole-2-carboxylic acid, 5-[2-[2-[3-(trifluoromethyl)phenyl]-2-hydroxy-ethylamino]-propyl]-1-[3-dimethylsulfamoyl-benzyl]-1H-indole-2-carboxylic acid, 5-[2-[2-phenyl-2-hydroxy-ethylamino]-propyl]-1-[3-dimethylsulfamoyl-benzyl]-1H-indole-2-carboxylic acid, 5-[2-[2-[6-aminopyridin-3-yl]-2-hydroxy-ethylamino]-propyl]-1-(3-dimethylsulfamoyl-benzyl]-1H-indole-2-carboxylic acid, 5-[2-[2-[6-amino-5-chloropyridin-3-yl]-2-hydroxy-ethylamino]-propyl]-1-[3-dimethylsulfamoyl-benzyl]-1H-indole-2-carboxylic acid, 5-[2-[2-[6-amino-5-cyanopyridin-3-yl]-2-hydroxy-ethylamino]-propyl]-1-[3-dimethylsulfamoyl-benzyl]-1H-indole-2-carboxylic acid, 5-[2-[2-[6-aminopyrimidin-3-yl]-2-hydroxy-ethylamino]-propyl]-1-[3-dimethylsulfamoyl-benzyl]-1H-indole-2-carboxylic acid, 5-[2-[2-hydroxy-3-phenoxy-propylamino]-propyl-1-[3-dimethylsulfamoyl-benzyl]-1H-indole-2-carboxylic acid, 5-[2-[2-[3-bromophenyl]-2-hydroxy-ethylamino]-propyl]-1-[4-dimethylsulfamoyl-benzyl]-1H-indole-2-carboxylic acid, 5-[2-[2-[3-(trifluoromethyl)phenyl]-2-hydroxy-ethylamino]-propyl]-1-[4-dimethylsulfamoyl-benzyl]-1H-indole-2-carboxylic acid, 5-[2-[2-phenyl-2-hydroxy-ethylamino]-propyl]-1-[4-dimethylsulfamoyl-benzyl]-1H-indole-2-carboxylic acid, 5-[2-[2-[6-aminopyridin-3-yl]-2-hydroxy-ethylamino]-propyl]-1-[4-dimethylsulfamoyl-benzyl]-1H-indole-2-carboxylic acid, 5-[2-[2-[6-amino-5-chloropyridin-3-yl]-2-hydroxy-ethylamino]-propyl]-1-[4-dimethylsulfamoyl-benzyl]-1H-indole-2-carboxylic acid, 5-[2-[2-[6-amino-5-cyanopyridin-3-yl]-2-hydroxy-ethylamino]-propyl]-1-[4-dimethylsulfamoyl-benzyl]-1H-indole-2-carboxylic acid, 5-[2-[2-[6-aminopyrimidin-3-yl]-2-hydroxy-ethylamino]-propyl]-1-[4-dimethylsulfamoyl-benzyl]-1H-indole-2-carboxylic acid, 5-[2-[2-[3-chlorophenyl]-2-hydroxy-ethylamino]-propyl]-1-[3-trifluoromethylsulfamoyl-benzyl]-1H-indole-2-carboxylic acid, 5-[2-[2-[3-bromophenyl]-2-hydroxy-ethylamino]-propyl]-1-[3-trifluoromethylsulfamoyl-benzyl]-1H-indole-2-carboxylic acid, 5-[2-[2-[3-(trifluoromethyl)phenyl]-2-hydroxy-ethylamino]-propyl]-1-[3-trifluoromethylsulfamoyl-benzyl]-1H-indole-2-carboxylic acid, 5-[2-[2-phenyl-2-hydroxy-ethylamino]-propyl]-1-[3-trifluoromethylsulfamoyl-benzyl]-1H-indole-2-carboxylic acid, 5-[2-[2-[6-aminopyridin-3-yl]-2-hydroxy-ethylamino]-propyl]-1-[3-trifluoromethylsultamoyl-benzyl]-1H-indole-2-carboxylic acid, 5-[2-[2-[6-amino-5-chloropyridin-3-yl]-2-hydroxy-ethylamino]-propyl]-1-[3-trifluoromethylsulfamoyl-benzyl]-1H-indole-2-carboxylic acid, 5-[2-[2-[6-amino-5-cyanopyridin-3-yl]-2-hydroxy-ethylamino]-propyl]-[3-trifluoromethylsulfamoyl-benzyl]-1H-indole-2-carboxylic acid, 5-[2-[2-[6-aminopyrimidin-3-yl]-2-hydroxy-ethylamino]-propyl]-1-[3-trifluoromethylsulfamoyl-benzyl]-1H-indole-2-carboxylic acid, 5-[2-[2-hydroxy-3-phenoxy-propylamino]-propyl-1-[3-trifluoromethylsulfamoyl-benzyl]-1H-indole-2-carboxylic acid, 5-[2-[2-[3-chlorophenyl]-2-hydroxy-ethylamino]-propyl]-1-[4-trifluoromethylsulfamoyl-benzyl]-1H-indole-2-carboxylic acid, 5-[2-[2-[3-bromophenyl]-2-hydroxy-ethylamino]-propyl]-1-[4-trifluoromethylsulfamoyl-benzyl]-1H-indole-2-carboxylic acid, 5-[2-[2-[3-(trifluoromethyl)phenyl]-2-hydroxy-ethylamino]-propyl]-1-[4-trifluoromethylsulfamoyl-benzyl]-1H-indole-2-carboxylic acid, 5-[2-[2-phenyl-2-hydroxy-ethylamino]-propyl]-1-[4-trifluoromethylsulfamoyl-benzyl]-1H-indole-2-carboxylic acid, 5-[2-[2-[6-aminopyridin-3-yl]-2-hydroxy-ethylamino]-propyl]-1-[4-trifluoromethylsulfamoyl-benzyl]-1H-indole-2-carboxylic acid, 5-[2-[2-[6-amino-5-chloropyridin-3-yl]-2-hydroxy-ethylamino]-propyl]-1-[4-trifluoromethylsulfamoyl-benzyl]-1H-indole-2-carboxylic acid, 5-[2-[2-[6-amino-5-cyanopyridin-3yl]-2-hydroxy-ethylamino]-propyl]-1-[4-trifluoromethylsulfamoyl-benzyl]-1H-indole-2-carboxylic acid, 5-[2-[2-[6-aminopyrimidin-3-yl]-2-hydroxy-ethylamino]-propyl]-1-[4-trifluoromethylsulfamoyl-benzyl]-1H-indole-2-carboxylic acid, 5-[2-[2-hydroxy-3-phenoxy-propylamino]-propyl-1-[4-trifluoromethylsulfamoyl-benzyl]-1H-indole-2-carboxylic acid, 5-[2-[2-[3-chlorophenyl]-2-hydroxy-ethylamino]-propyl]-1-[3-[methyl-trifluoromethyl-sulfamoyl]-benzyl]-1H-indole-2-carboxylic acid, 5-[2-[2-[3-bromophenyl]-2-hydroxy-ethylamino]-propyl]-1-[3-[methyl-trifluoromethyl-sulfamoyl]-benzyl]-1H-indole-2-carboxylic acid, 5-[2-[2-[3-(trifluoromethyl)phenyl]-2-hydroxy-ethylamino]-propyl]-1-[3-[methyl-trifluoromethyl-sulfamoyl]-benzyl]-1H-indole-2-carboxylic acid, 5-[2-[2-phenyl-2-hydroxy-ethylamino]-propyl]-1-[3-[methyl-trifluoromethyl-sulfamoyl]-benzyl]-1H-indole-2-carboxylic acid, 5-[2-[2-[6-aminopyridin-3-yl]-2-hydroxy-ethylamino]-propyl]-1-[3-[methyl-trifluoromethyl-sulfamoyl]-benzyl]-1H-indole-2-carboxylic acid, 5-[2-[2-[6-amino-5-chloropyridin-3-yl]-2-hydroxy-ethylamino]-propyl]-1-[3-[methyl-trifluoromethyl-sulfamoyl]-benzyl]-1H-indole-2-carboxylic acid, 5-[2-[2-[6-amino-5-cyanopyridin-3-yl]-2-hydroxy-ethylamino]-propyl]-1-[3-trifluoromethyl-sulfamoyl]-benzyl]-1H-indole-2-carboxylic acid, 5-[2-[2-[6-aminopyrimidin-3-yl]-2-hydroxy-ethylamino]-propyl]-1-[3-[methyl-trifluoromethyl-sulfamoyl]-benzyl]-1H-indole-2-carboxylic acid, 5-[2-[2-hydroxy-3-phenoxy-propylamino]-propyl-1-[3-[methyl-trifluoromethyl-sulfamoyl]-benzyl]-1H-indole-2-carboxylic acid, 5-[2-[2-[3-chlorophenyl]-2-hydroxy-ethylamino]-propyl]-1-[4-[methyl-trifluoromethyl-sulfamoyl]-benzyl]-1H-indole-2-carboxylic acid, 5-[2-[2-[3-bromophenyl]-2-hydroxy-ethylamino]-propyl]-1-[4-[methyl-trifluoromethyl-sulfamoyl]-benzyl]-1H-indole-2-carboxylic acid, 5-[2-[2-[3-(trifluoromethyl)phenyl]-2-hydroxy-ethylamino]-propyl]-1-[4-[methyl-trifluoromethyl-sulfamoyl]-benzyl]-1H-indole-2-carboxylic acid, 5-[2-[2-phenyl-2-hydroxy-ethylamino]-propyl]-1-[4-[methyl-trifluoromethyl-sulfamoyl]-benzyl]-1H-indole-2-carboxylic acid, 5-[2-[2-[6-aminopyridin-3-yl]-2-hydroxy-ethylamino]-propyl]-1-[4-[methyl-trifluoromethyl-sulfamoyl]-benzyl]-1H-indole-2-carboxylic acid, 5-[2-[2-[6-amino-5-chloropyridin-3-yl]-2-hydroxy-ethylamino]-propyl]-1-[4-[methyl-trifluoromethyl-sulfamoyl]-benzyl]-1H-indole-2-carboxylic acid, 5-[2-[2-[6-amino-5-cyanopyridin-3-yl]-2-hydroxy-ethylamino]-propyl]-1-[4-[methyl-trifluoromethyl-sulfamoyl]-benzyl]-1H-indole-2-carboxylic acid, 5-[2-[2-[6-aminopyrimidin-3-yl]-2-hydroxy-ethylamino]-propyl]-1-[4-[methyl-trifluoromethyl-sulfamoyl]-benzyl]-1H-indole-2-carboxylic acid, 5-[2-[2-hydroxy-3-phenoxy-propylamino]-propyl-1-[4-[methyl-trifluoromethyl-sulfamoyl]-benzyl]-1H-indole-2-carboxylic acid.

The present invention also relates to a pharmaceutical composition for treating a condition selected from the group consisting of diabetes, hyperglycemia and obesity in a mammal, comprising an amount of a compound of formula I, or a pharmaceutically acceptable salt thereof, effective in treating such condition and a pharmaceutically acceptable carrier.

The present invention also relates to a method of treating a condition selected from the group consisting of diabetes, hyperglycemia and obesity in a mammal, comprising administering to a mammal in need of such treatment an amount of a compound of formula I, or a pharmacetically acceptable salt thereof, effective in treating or preventing such condition.

The present invention also relates to a pharmaceutical composition for treating a condition selected from the group consisting of diabetes, hyperglycemia and obesity in a mammal, comprising a $\beta_3$-adrenoceptor stimulating amount of a compound of formula I, or a pharmaceutically acceptable salt thereof, and a pharmaceutically acceptable carrier.

The present invention also relates to a method of treating a condition selected from the group consisting of diabetes, hyperglycemia and obesity in a mammal, comprising administering to a mammal in need of such treatment a $\beta_3$-adrenoceptor stimulating amount of a compound of formula I, or a pharmaceutically acceptable salt thereof.

The present invention also relates to a pharmaceutical composition for increasing the content of lean meat in edible animals, comprising a $\beta_3$-adrenoceptor stimulating amount of a compound of formula I, or a pharmaceutically acceptable salt thereof, and a pharmaceutically acceptable carrier.

The present invention also relates to a method of increasing the content of lean meat in edible animals comprising administering to an edible animal a $\beta_3$-adrenoceptor stimulating effective amount of a compound of formula I, or an acceptable salt thereof.

This invention includes prodrugs of compounds of formula I having free amino, amido, hydroxy or carboxylic groups. Prodrugs are understood to comprise an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs are also understood to include carbonates, carbamates, amides and alkyl esters which are covalently bonded to the above substituents of formula I through the carbonyl carbon prodrug sidechain. Prodrugs also include compounds in which the secondary amine and its β-hydroxy when taken together form a group of the formula

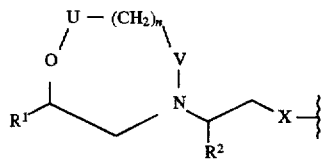

wherein n, $R^1$, $R^2$ and X are as defined in formula I and U and V are independently carbonyl, methylene, $SO_2$ or $SO_3$, wherein methylene is optionally substituted with hydroxy.

The present invention also relates to the pharmaceutically acceptable acid or base addition salts of compounds of the formula I. The acids which are used to prepare the pharmaceutically acceptable acid addition salts of the aforementioned base compounds of this invention are those which form non-toxic acid addition salts, e.g., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate,saccharate, benzoate, methanesulfonate, ethanesulfonate, benzenesulfonate, p-toluenesulfonateandpamoate (i.e., 1,1'-methylene-bis-(2-hydroxy-3-naphthoate)) salts. Examples of pharmaceutically acceptable base addition salts are the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

The term "treating" as used herein includes preventative treatment.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The processes and products of the present invention are illustrated in the following reaction schemes. Except where otherwise indicated, in the reaction scheme and discussion that follow, formulas I, II, III, IV, and V, and substituents $R^1$, $R^2$, $R^3$, $R^4$, $R^5$, $R^6$, $R^7$, $R^8$, $R^9$, X and halogen are defined as above.

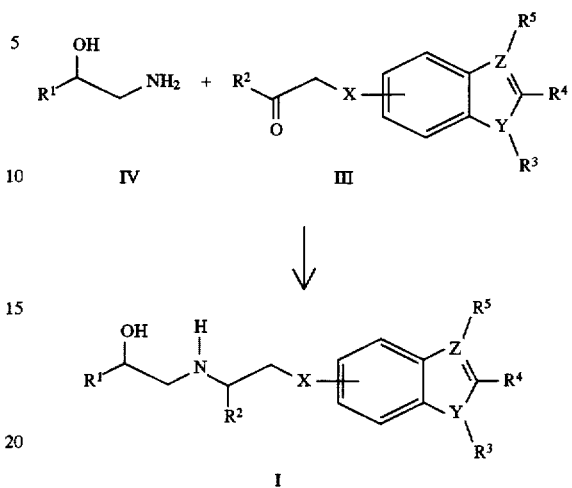

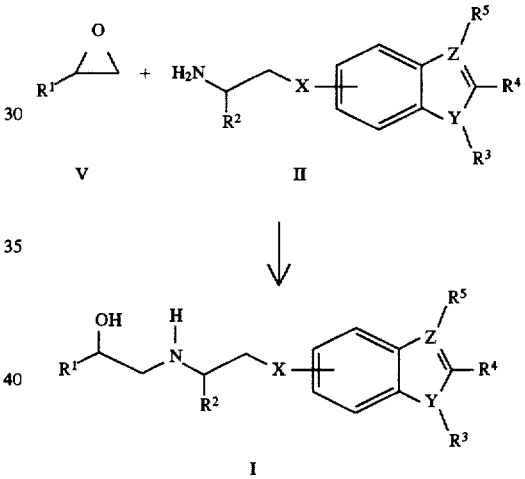

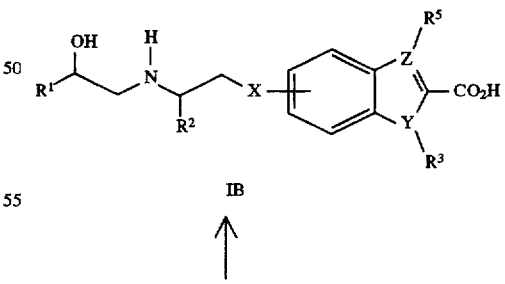

5,767,133
23
-continued
SCHEME 3
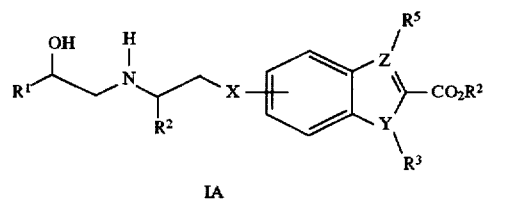
IA
↓
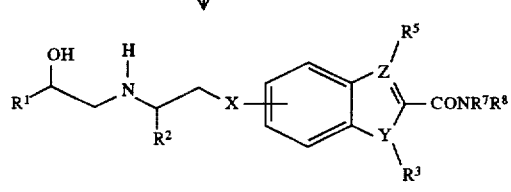
IC
SCHEME 4
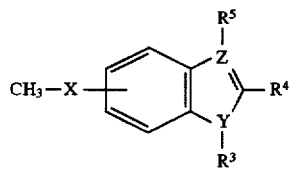
↓
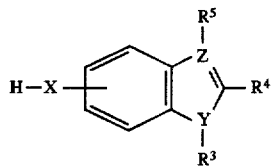
↓
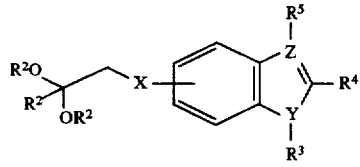
↓
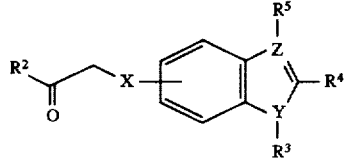
↓
24
-continued
SCHEME 4
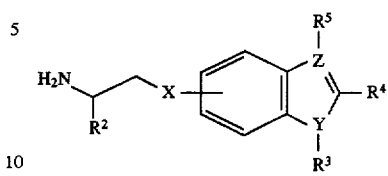   II
SCHEME 5
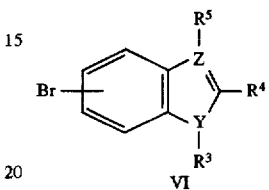
VI
↓
XV   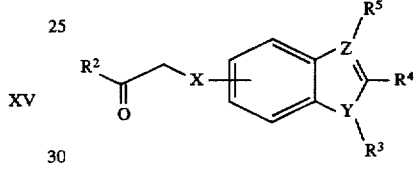
III
↓
XVI   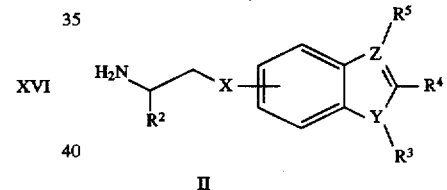
II
SCHEME 6
XVII   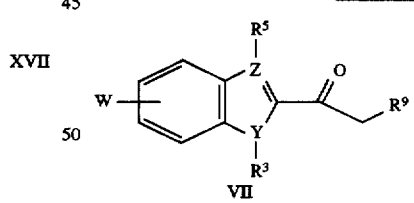
VII
↓
III   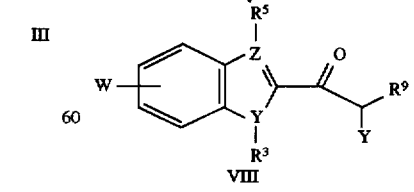
VIII
↓

25

-continued
SCHEME 6

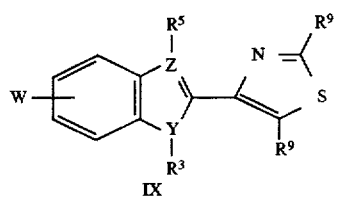

26

Referring to Scheme 2, a compound of formula I can be synthesized from compounds of formula II by reaction with an epoxide of the formula V. This reaction is typically carried out by reacting an amine of formula II with an epoxide of formula V in a polar aprotic solvent such as dimethyl sulfoxide, dimethyl formamide, acetonitrile or a lower alkanol such as ethanol, isopropanol or butanol, at a temperature from about −10° C. to about 125° C. Preferably the solvent is dimethyl sulfoxide and the reaction is run at a temperature from about 0° C. to about 10° C.

A preferred modification of the above reaction involves pretreatment of the amine of formula II with N-(trimethyl-

SCHEME 7

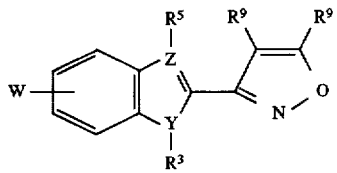

XI

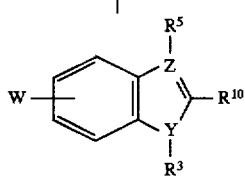

X

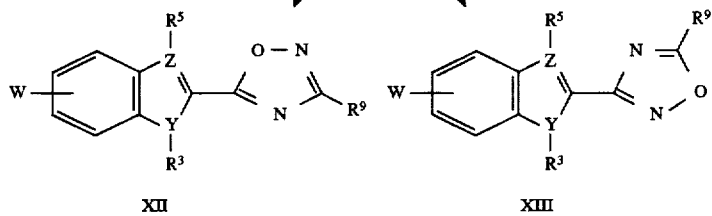

XII                              XIII

Scheme 1 illustrates the preparation of compounds of the formula I from aldehydes or ketones of formula III.

Referring to Scheme 1, a compound of the formula III is reacted with a compound of the formula IV to produce a compound of the formula I. This reaction is typically carried out in the presence of a reducing agent such as sodium cyanoborohydride, sodium triacetoxyborohydride, sodium borohydride, hydrogen and a metal catalyst, zinc and hydrochloric acid, or borane dimethyl sulfide followed by treatment with formic acid. It is generally conducted at temperatures from about −60° C. to about 50° C. Suitable reaction inert solvents for this reaction include lower alcohols (e.g., methanol, ethanol and isopropanol), acetic acid, chlorinated hydrocarbon solvents (e.g., methylene chloride, chloroform, 1,2 dichloroethane) and tetrahydrofuran (THF). Preferably, the solvent is 1,2-dichloroethane, the temperature is about 250° C., and the reducing agent is sodium triacetoxyborohydride.

Scheme 2 illustrates an alternative method for the preparation of compounds of formula I from amines of formula 11.

silyl)-acetamide to form a silyated compound of the formula

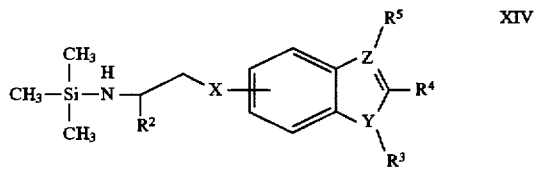

This reaction is typically carried out in a polar aprotic solvent such as dimethyl sulfoxide, dimethyl formamide, acetonitrile or a lower alkanol such as ethanol, isopropanol or butanol, at a temperature from about −100° C. to about 125° C. Preferably, the silyation is carried out at about 25° C. and the reaction with the epoxide is accomplished at about 60° C. After silyation is complete, the compound of formula XIV is reacted with the epoxide of formula V as described above.

Scheme 3 illustrates the preparation of compounds of formulae IB and IC from compounds of formula IA. Compounds of formulae IB and IC are compounds of formula I in which $R^4$ is $CO_2H$ and $CO_2NR^7R^8$, respectively. Compounds of formula IA are compounds of formula I wherein $R^4$ is $CO_2R^2$. Compounds of formula IA are prepared by the methods of Schemes 1 and 2. The transformations depicted in scheme 3 may be accomplished by methods well known to those skilled in the art.

Referring to Scheme 3, compounds of formula IA can be converted into carboxylic acids of formula IB by treatment with an acid or a base. Examples of suitable bases for the reaction are: sodium hydroxide (NaOH), potassium hydroxide (KOH), and lithium hydroxide. Suitable acids for the reaction include: hydrochloric acid (HCl), hydrobromic acid and sulfuric acid. Preferably, the base is potassium hydroxide. The solvent for the aforesaid process is typically a lower alkanol, hexane, DMF, toluene and/or water. The lower alkanol can be methanol, ethanol, propanol or butanol. The reaction temperature may range from about 0° C. to about 100° C. Preferably, the temperature is about 25° C.

Compounds of formula IA can be converted into other esters of the formula IA, in which a different definition of $R^2$ has been substituted, by transesterification. Transesterification is facilitated by reacting a compound of formula IA with acid or base in an excess of an alcohol of the formula $R^2OH$. Suitable acids for the reaction include hydrochloric, hydrobromic, sulfuric and toluene sulfonic acid. Preferably, the acid is hydrochloric acid. The reaction temperature may range from about 0° C. to about 115° C. Suitable solvents include alcohols of formula $R^2OH$, and mixtures thereof with toluene, cyclohexane, DMF and methylene chloride.

Alternatively, compounds of formula IA can be converted into amides of formula IC by treatment of the ester of formula IA with an amine of the formula $R^7R^8NH$. Usually, a polar protic solvent such as a lower alkanol is used, and the reaction is run at a temperature from about 0° C. to about 125°° C. for about 0.5 to about 24 hours. Suitable solvents include lower alcohols, and mixtures thereof with toluene, cyclohexane, DMF and methylene chloride. Preferably, the reaction is conducted in methanol at about 650° C. for about 3 to about 24 hours.

Scheme 4 refers to the preparation of compounds of the formulae II and III, wherein X is O or S. Compounds of formulae II and III are the starting materials for the synthesis of compounds of formula I in Schemes 1 through 3. Compounds of formula III, wherein X is O or S, can be used to form compounds of formula I according to the processes of Scheme 1. Compounds of formula II, wherein X is O or S, can be used to form compounds of formula I according to the processes of Scheme 2.

Referring to Scheme 4, compounds of formula II are made by reductive amination of a compound of formula III. The conditions for reductive amination are as described above for the conversion of the ketone of formula III to the compound of formula I in Scheme I, with the exception that the amine used is ammonia or an acid addition salt thereof, instead of the amine of formula IV.

Compounds of formula III can be made in three steps beginning with compounds of the formula XV.

Compounds of the formula XV are first converted to thiols or phenols of the formula XVI by treatment of an ether (when X is O) or a thioether (when X is S) of formula XV with boron tribromide. Suitable solvents for the aforesaid reaction are non-polar aprotic solvents such as methylene chloride, toluene, chloroform, or carbon tetrachloride. Preferably, the solvent is methylene chloride. The temperature of the reaction may range from about −78° C. to about 20° C. during the reaction with boron tribromide. It is preferably about 0°C.

The thiol or phenol of formula XVI so formed is converted into a ketal or acetal of the formula XVII by treatment with a compound of the formula

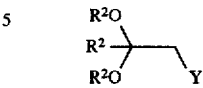

wherein Y is chloro, bromo or iodo, in the presence of a base. Preferably, the thiol or phenol of formula XVI is first converted into an anion by reaction with a base. Examples of appropriate bases include sodium hydride and potassium t-butoxide. The preferred base is sodium hydride (NaH). Examples of suitable solvents for the aforesaid process include polar aprotic solvents such as dimethyl formamide, dimethylsulfoxide, and sulfolane. Preferably, the solvent is dimethyl formamide.

The temperature for the aforesaid reaction is in the range of about −10° C. to about 100° C. Preferably, the temperature is 30° C.

The ketal or acetal of formula XVII so formed is converted into the corresponding compound of formula III by reaction with an acid. Typically, this reaction is conducted at a temperature in the range of about 10° C. to about 100° C. Examples of appropriate acids for the aforesaid process are hydrochloric, hydrobromic and sulfuric acids. Preferably, the acid is hydrochloric acid. Suitable solvents for the aforesaid process include polar solvents such as acetone and/or water. Preferably, the solvent is acetone.

Scheme 5 refers to the preparation of compounds of the formulae III and II wherein X is a direct link. Compounds of the formulae III and II are starting materials for the synthesis of the compounds of the invention illustrated in Schemes 1through 3.

Compounds of formula III, wherein X is a direct link, can be used to form compounds of formula I according to the processes of Scheme 1.

Compounds of the formula III, wherein X is a direct link, can be used to form compounds of the formula I according to the processes of Scheme 2.

Referring to Scheme 5, compounds of the formula III can be converted into compounds of the formula II by reductive amination of a compound of the formula III with ammonia as described in Scheme 1.

Compounds of the formula III are prepared from compounds of the formula VI, by treatment of a compound of the formula VI with a tin reagent of the formula $R^2COCH_2Sn(CH_3CH_2CH_2CH_3)_3$ in the presence of palladium (II) acetate and tri-o-tolylphosphine. The tin reagent, $R^2COCH_2Sn(CH_3CH_2CH_2CH_3)_3$, is formed by reaction of tributyltin methoxide with a compound of the formula

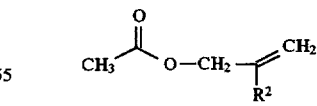

Suitable solvents for the aforesaid process include nonpolar solvents such as toluene, benzene and hexane. Preferably, the solvent is toluene. The temperature for the aforesaid process is generally in the range of about 10° C. to about 150° C., and is preferably about 95° C.

Scheme 6 refers to the preparation of compounds of formula IX, wherein W is bromo, $-OCH_3$ or $-SCH_3$. Compounds of formula IX wherein W is bromo are compounds of formula VI in Scheme 5, wherein $R^4$ is a group of the formula

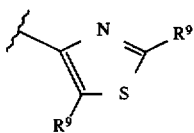

Compounds of formula IX wherein W is —OCH₃ or —SCH₃ are compounds of formula XV in Scheme 4, wherein X is oxygen or sulfur and $R^4$ is a group of the formula

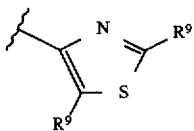

Referring to Scheme 6, a compound of formula IX is formed in two steps beginning with a compound of formula VII. The compound of formula VII is reacted with a suitable halogenating agent such as liquid bromine, N-bromosuccinimide, N-chlorosuccinimide or chlorine gas in the presence of light to form an α-haloketone of the formula VIII wherein Y is chloro, bromo or iodo. This reaction is typically carried out in a solvent such as carbon tetrachloride, chloroform or methylene chloride, preferably carbon tetrachloride, at a temperature from about 10° C. to about 100° C., preferably about 30° C.

The α-haloketone of formula VIII is converted into the thiazole of formula IX by reaction of the α-haloketone of formula VIII with a thioamide of the formula

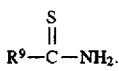

This reaction is typically carried out in a polar protic solvent such as a lower alkanol, DMF, DMSO, or digylme. Suitable alcohols include methanol, ethanol, propanol and butanol. The reaction temperature may range from about 20° C. to about 150° C. Preferably, the reaction is carried out in ethanol at a temperature of about 80° C.

Scheme 7 refers to the preparation of compounds of the formulae XI, XII and XIII wherein W is bromo, —OCH₃ or —SCH₃. Compounds of the formula XI wherein W is bromo are compounds of formula VI in Scheme 5 wherein $R^4$ is

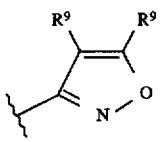

Compounds of formula XI wherein W is —OCH, or —SCH, are compounds of formula XV in Scheme 4 wherein X is oxygen or sulfur and $R^4$ is

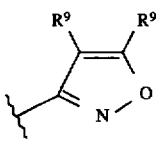

Compounds of formula XII wherein W is bromo are compounds of formula VI in Scheme 5 wherein $R^4$ is

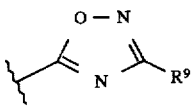

Compounds of formula XII wherein W is —OCH₃ or —SCH₃ are compounds of formula XV in Scheme 4 wherein X is oxygen or sulfur and $R^4$ is

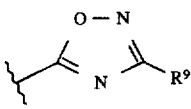

Compounds of formula XIII wherein W is bromo are compounds of formula VI in Scheme 5 wherein $R^4$ is

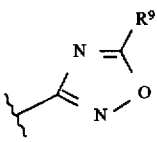

Compounds of formula XIII wherein W is —OCH₃ or —SCH₃ are compounds of formula XV in Scheme 4 wherein X is oxygen or sulfur and $R^4$ is

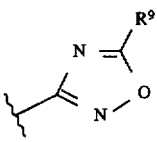

Referring to Scheme 7, compounds of formula X wherein $R^{10}$ is —COCH₂R⁹ are converted into isoxazoles of formula XI by a two step process. Compounds of formula X are first converted into oximes of the formula

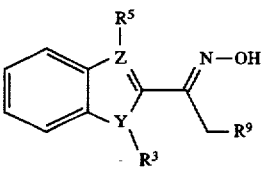

XVIII by treatment of the ketone of formula X with hydroxylamine in a polar solvent such as a lower alkanol and/or water. Suitable alcohols include methanol, ethanol and isopropanol. The reaction temperature may range from about 20° C. to about 100° C.

The oxime of formula XVIII is converted into the isoxazole of formula XI by reaction with two equivalents of a strong base such as lithium diisopropyl amide, phenyl lithium or N-butyl lithium, followed by addition of an amide of the formula

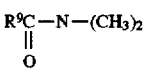

and subsequent cyclization with hydrochloric acid in dioxane at reflux. Modifications of this process are described in G. N. Barber, *Journal of Organic Chemistry*, 43, 3015–3021 (1978).

Scheme 7 also describes the synthesis of 3,5-disubstituted-1,2,4-oxadiazoles of formula XII from compounds of formula X, wherein $R^{10}$ is an ester equivalent of formula —$COR^{11}$, and wherein $R^{11}$ is halo or alkoxy. The ester of formula X is reacted with an amidoxime of the formula

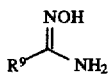

to form the oxadiazole of formula XII, according to the procedure described in Swain et al., *J. Med. Chem.* 34, 140–151 (1991).

Scheme 7 also describes the synthesis of 3,5 disubstituted 1,2,4-oxadiazoles of formula XIII. Oxadiazoles of formula XIII can be synthesized by reacting compounds of formula X, wherein $R^{10}$ is an amidoxime of the formula

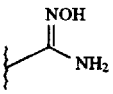

with an ester equivalent (i.e. $R^9COCl$) or a compound of the formula $R^9C(OR^2)_3$ according to the procedure of Shine et al., *J. Heterocyclic Chem.*, 26, 125–128 (1989).

The pharmaceutically-acceptable cation salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention may be prepared by conventional peptide coupling reactions coupling a free amino or carboxylic group of the compound of formula I with an amino acid or a polypeptide, e.g. dipeptide, chain. The coupling reaction is generally conducted at a temperature of about −30° to about 80° C., preferably about 0° to about 25° C. Suitable coupling reagents are usually present, such as dicyclohexylcarbodiimide with hydroxybenzotriazole (HBT), N-3-dimethylaminopropyl-N′-ethylcarbodiimide with HBT, 2-ethoxy-1-ethoxycarbonyl-1,2-dihydroquinoline, carbonyl diimidazole with HBT, or diethylphosphoryl-cyanide. The reaction is generaly conducted in an inert solvent such as acetonitrile, methylene chloride, chloroform, dimethylformamide, dioxane, tetrahydrofuran, dimethoxyethane, or water, or a mixture of two or more such solvents.

Ester, carbonate or carbamate prodrugs of this invention may be prepared by reaction of a free hydroxyl or amino group of the compound of formula I with an activated carbonyl containing molecule such as acetyl chloride or ethyl chloroformate. The reaction can be carried out neat or in the presence of a reaction inert solvent such as methylene chloride, at a temperature from about −78° to about 100° C. Alcohols can also be reacted with cyanogen chloride in the presence of a Lewis acid to form carbamates. Ester and amide prodrugs of free carboxylic acid groups can be made according to the methods of scheme 3.

Prodrugs in which the secondary amine and its β hydroxy, taken together, form a group of the formula

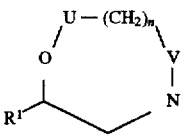

are formed by methods analogous to those described in U.S. Pat. No. 4,593,023 to Beecham issued on Jun. 3, 1986, European Patent Application 170,135A to Beecham published on Jul. 21, 1984 and U.S. Pat. No. 4,607,033 issued on Aug. 19, 1986 to Beecham.

When treating diabetes mellitus and/or hyperglycemia generally satisfactory results are obtained when the compounds of the formula (I) and the pharmaceutically acceptable salts thereof (hereinafter also referred to as "the active compounds of the present invention") are administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 50 mg/kg body weight of the subject per day, preferably about 0.1 to about 25 mg/kg body weight per day, administered singly or as a divided dose. However, the optimum dosage for the individual subject being treated will be determined by the person responsible for the treatment, generally smaller doses being administered initially and thereafter increments made to determine the most suitable dosage. This will vary according to the particular compound employed and with the subject being treated.

When treating obesity, in conjunction with diabetes and/or hyperglycemia, or alone, generally satisfactory results are obtained when the compounds of the present invention are administered at a daily dosage of from 0.01 milligram to about 50 milligrams per kilogram of animal body weight, preferably given in divided doses 4 times a day, or in sustained release form. For most large mammals, the total daily dosage is from about 0.1 milligrams to about 6000 milligrams, preferably from about 1 milligrams to about 1500 milligrams. In the case of a 70 kg adult human, the total daily dose will generally be from about 0.1 milligrams to about 1500 milligrams. This dosage regimen may be adjusted to provide the optimal therapeutic response.

The compounds of the present invention are used in combination with a pharmaceutically acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in man.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The effective dosage of the active ingredient employed may vary depending on the particular compound employed, the mode of administration, the condition being treated and the severity of the condition being treated.

The compounds of the present invention also possess utility for increasing lean meat deposition and/or improving lean meat to fat ratio in edible animals, i.e., ungulate animals and poultry.

Animal feed compositions effective for increasing lean meat deposition and for improving lean meat to fat ratio in poultry, swine, sheep, goats, domestic pets and cattle are generally prepared by mixing the compounds of the present invention with a sufficient amount of animal feed to provide from about $10^{-3}$ to 500 ppm of the compound in the feed.

Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, can molasses, urea, bone meal, corncob meal and the like. The carrier promotes a uniform distribution of the active ingredients in the finished feed into which the supplement is blended. It thus performs an important function by ensuring proper distribution of the active ingredient throughout the feed.

If the supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed.

The preferred poultry and domestic pet feeds usually contain about 0.01 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the present invention to provide the animal with 0.01 to 100 mg/kg/day of body weight of the active ingredient. The preferred dosage for swine, cattle, sheep and goats is in the range of from 0.01 to 50 mg/kg/day of body weight of active ingredient; whereas, the preferred dose level for poultry and domestic pets is usually in the range of from 0.01 to 35 mg/kg/day of body weight.

Paste formulations can be prepared by dispersing the active compound in a pharmaceutically acceptable oil such as peanut oil, sesame oil, corn oil or the like.

Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantageous features. For the pet owner or veterinarian who wishes to increase leanness and trim unwanted fat from pet animals, the present invention provides the means by which this can be accomplished. For the poultry men and swine raisers, using the method of the present invention yields leaner animals which command higher prices from the meat industry.

METHODS

The compounds of this invention may be tested for hypoglycemic activity according to the following procedure.

Five to eight week old C57 BL/6J-ob/ob mice (obtained from Jackson Laboratory, Bar Harbor, Maine) are housed five per cage under standard animal care practices. After a one week acclimation period, the animals are weighed and 25 microliters of blood is collected via an ocular bleed prior to any treatment. The blood sample is immediately diluted 1:5 with saline containing 2.5 mg/ml sodium fluoride and 2% sodium heparin, and held on ice for metabolite analysis. Animals are then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs are administered in a vehicle consisting of 0.25% w/v methyl cellulose. On day 5, the animals are weighed again and bled (via the ocular route) for blood metabolite levels. The freshly collected samples are centrifuged for two minutes at 10,000 xg at room temperature. The supernatant is analyzed for glucose, for example, by the ABA 200 Bichromatic Analyzer™[1], using the A-gent™ glucose UV reagent system[2] (hexokinase method) using 20, 60 and 100 mg/dl standards. Plasma glucose is then calculated by the equation,

*Plasma glucose (mg/dl)=Sample value×5×1.67=8.35×Sample value* where 5 is the dilution factor and 1.67 is the plasma hematocrit adjustment (assuming the hematocrit is 40%).

[1] A registered trademark of Abbott Laboratories, Diagnostics Division, 820 Mission Street, So. Pasadena, Calif. 91030.
[2] A modification of the method of Richterrich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Selectivity of a compound for $\beta_3$-receptors over $\beta_2$ and $\beta_1$ receptors may be determined using the following procedures.

In vitro selectivity may be determined by measurement of cyclic Adenosine mono-phosphate (cAMP) on Chinese hamster ovary cells. Chinese hamster ovary cells uniquely transfected with the gene for the human $\beta_1$, $\beta_2$ or $\beta_3$ receptor are grown to confluence in Ham's F12 media containing 10% fetal bovine serum, 500 µg/ml Geneticin, 100 U/mt penicillin, 100 µg/ml streptomycin and 250 ng/ml Fungizone. Compounds are dissolved in Hams F12 media, and added to the cells at $10^{-10}$–$10^{-5}$M along with $10^{-3}$M isobutylmethylxanthine to inhibit phosphodiesterase activity. The media and cells are then incubated for 10 minutes at 37° C. At the end of this period, the media is aspirated, the cells dissolved in 0.01 N HCl and then the media is neutralized with 1N NaOH. The cellular content of cAMP can then be determined by Radioisotope Analysis (RIA) using a kit from New England Nuclear. There is a direct correlation between the cellular content of cAMP and the agonism of the $\beta_3$ receptor.

In vivo efficacy and thermogenic activity may be determined by measurement of oxygen consumption and ambulatory activity on male Sprague-Dawley rats. Whole animal oxygen consumption may be measured using an open circuit, indirect calorimeter (Oxymax™, from Columbus Instruments). The Oxymas gas sensors are calibrated with nitrogen ($N_2$) gas and gas mixture (0.5% carbon dioxide ($CO_2$), 20.5% oxygen ($O_2$), 79% $N_2$; Linde Specialty gases) before each experiment. Rats (male, Sprague Dawley, 300–380 g body weight) are placed in sealed chambers (43×43×10 cm) of the calorimeter and the chambers placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken (repeated interruptions of the same beam are not registered) and the results are recorded as counts. Basal oxygen consumption and ambulatory activity can be measured every 10 minutes for 2.5 to 3 hours. At the end of the basal period, the chambers are opened and the test compound (0.01 to 10 mg/kg, prepared in saline) or an equivalent volume of saline is administered by oral gavage. Oxygen consumption and ambulatory activity can be measured every 10 minutes for an additional three hours postdosing. Percent change in oxygen consumption may be calculated by averaging the post-dosing values for 2.5 hours and dividing by basal oxygen consumption (average of the predosing values except the first hour). Oxygen consumption values obtained during time periods where ambulatory activity exceeded 100 counts are excluded from the calculation. Thus, the values represent % change in resting oxygen consumption.

In vivo selectivity for $\beta_1$ and $\beta_2$ adrenoceptors may be determined by measurements of heart rate and blood pressure gathered on rats (male, Sprague Dawley, 300–380 g body weight) anesthetized with pentobarbital (50–60 mg/kg, i.p.). The left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure were measured by attaching the catheter to a pressure transducer and the results recorded on a Grass Model 7 polygraph. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes. To determine changes, basal values are subtracted from the average of the post dosing values.

All of the compounds of the invention were tested in the in vitro model and showed better than a four fold increase in cAMP levels at a dose of 10 nM.

The present invention is illustrated by the following Examples. However, it should be understood that the invention is not limited to the specific details of these examples.

EXAMPLES

Procedure A

Methyl 5-hydroxybenzofuran-2-carboxylic acid

To a stirred solution of ethyl 5-methoxybenzofuran-2-carboxylic acid (5.0 g, 26 mmol) in dichloromethane ($CH_2Cl_2$) (100 mL) at 0 ° C. was added boron tribromide (8.6 mL, 91 mmol) and the resulting dark solution was allowed to stir at room temperature for 2 hours. The reaction solution was poured over ice, stirred for 30 minutes and extracted with ethyl acetate, (EtOAc). The organic phase was washed with water, saturated aqueous brine, dried over sodium sulfate, ($Na_2SO_4$), and concentrated in vacuo to afford 5-hydroxybenzofuran-2-carboxylic acid (4.0 g; m.p. 223–228° C.).

Gaseous hydrochloric acid was bubbled into a cooled (0° C.), stirred solution of the above acid in methanol (50 mL) over a 15-min period. The resulting solution was then refluxed for 2.5 hours, and was then cooled and concentrated in vacuo. The residue was dissolved in ethyl acetate, washed with water, brine, dried (Na$_2$SO$_4$) and concentrated in vacuo. The resulting solids were flash chromatographed on silica gel (40% ethyl acetate:hexanes) to afford the title compound as a yellow solid, (3.3 g; m.p. 164–166C. Analytical Calculated for C$_{10}$H$_8$O$_4$:C, 62.52; H, 4.20. Found: C, 62.47; H, 4.09).

PROCEDURE B

Methyl 5-(2,2-dimethoxyethyloxy)benzofuran-2-carboxylic acid

To a stirred slurry of sodium hydride (0.11 g of 60% in oil, 2.7 mmol) in p-dioxane (10 mL) was added methyl 5-hydroxybenzofuran-2-carboxylic acid (0.5 g, 2.6 mmol) and the resulting green slurry was stirred at room temperature for 15 min. To this slurry was added a solution of bromoacetaldehyde dimethyl acetal (0.5 g, 3.0 mmol) in dimethylformamide (DMF) (10 mL) and the resulting solution was heated at reflux for 15 hours. The reaction mixture was poured into ethyl acetate, washed with water, brine, the organic phased dried (Na$_2$SO$_4$) and concentrated in vacuo. The resulting oil was flash chromatographed on silica gel (25% ethyl acetate:hexanes) to afford the title compound as a colorless solid, (0.16 g; m.p. 74–74° C.).

PRROCEDURE C

Methyl 5-(ethanal-2-oxy)benzofuran-2-carboxylic acid

A solution of methyl5-(2,2-dimethoxyethyloxy)benzofuran-2-carboxylic acid (0.16 g, 0.6 mmol) in acetone (4 mL) and 2 N aqueous hydrochloric acid (0.3 mL) was refluxed for 3.5 hours. The reaction solution was concentrated in vacuo, dissolved in ethyl acetate, washed with water, brine, dried (Na$_2$SO$_4$) and concentrated in vacuo to afford the title compound as a colorless solid, (0.14 g; m.p. 112–115° C.).

PROCEDURE D

Methyl 5-(propan-2-one-yl)benzofuran-2-carboxylic acid

A solution of methyl 5-bromobenzofuran-2-carboxylic acid (2.4 g, 9.3 mmol), tributyltin methoxide (4.0 mL, 14 mmol), isopropenyl acetate (1.4 mL, 14 mmol), palladium (II) acetate (0.1 g, 0.5 mmol) and tri-o-tolylphosphine (0.3 g, 1mmol) in toluene (6 mL) were heated at 95° C. for 2 hours. The reaction solution was concentrated in vacuo and subjected to flash chromatography on silica gel (25% ethyl acetate:hexanes) to afford the title compound as a colorless solid, (1.8 g; m.p. 77–79° C., Analytical Calculated for C$_{13}$H$_{12}$O$_4$:C, 67.25; H, 5.21. Found: C, 67.12; H, 4.95).

PROCEDURE E

5-Methoxy-2-(2-methyl-thiazol-4-yl)-benzofuran

A solution of 2-bromo-1-(5-methoxy-benzofuran-2-yl)-ethanone (0.6 g, 2.2 mmol) and thioacetamide (0.4 g, 5.1 mmol) in ethanol (15 mL) were refluxed for 1hour. The reaction mixture was concentrated in vacuo and subjected to flash chromatography on silica gel (14% ethyl acetate:hexanes) to afford the title compound as a solid, (0.47 g; m.p. 136–137° C.).

Example 1

Methyl 5-(2-(2(S)-hydroxy-3-phenoxy-propylamino) ethoxy)-benzofuran-2-carboxylic acid To a solution of methyl 5-(ethanal-2-oxy)benzofuran-2-carboxylic acid (0.13 g, 0.56 mmol) and 1-amino-3-phenoxypropan-2(S)-ol (0.10 g, 0.61 mmol) in dichloroethane (3 mL) was added glacial acetic acid (0.05 mL) and sodium triacetoxyborohydride (0.18 g, 0.83 mmol). After 2 hours, the reaction mixture was diluted into ethyl acetate, washed with saturated sodium bicarbonate, brine, the organic layer was dried (Na$_2$SO$_4$) and concentrated in vacuo. The resulting oil was subjected to flash chromatography (silica gel, 5% methanol: chloroform) to afford the title compound as an off-white solid, (0.10 g; m.p. 151–119° C., Analytical Calculated for C$_{21}$H$_{23}$NO$_6$·0.25H$_2$O: C, 64.70; H, 6.08; N, 3.59. Found: C, 64.89; H, 6.15; N, 3.51).

Example 2

Methyl 5-(2(R)-(2-(2-trifluoromethyl-thiazol-4-yl)-2(R)-hydroxyethyl-amino)-propyl)-benzofuran-2-carboxylic acid A solution of (R)-(2-trifluoromethyl-thiazol-4-yl)-ethylene oxide (0.20 g, 1.03 mmol) and methyl 5-(2(R)-2-aminopropyl)-benzofuran-2-carboxylic acid (0.20 g, 0.86 mmol) in isopropyl alcohol (1ml) was refluxed for 1.5 hours. After cooling, the reaction solution was concentrated in vacuo and the resulting oil was flash chromatographed (silica gel, 2% methanol:chloroform) to afford the title compound as an off-white solid (0.09 9); m.p. 99–100° C.

Example 3

5-(2-(2(S)-Hydroxy-3-phenoxy-propylamino) ethoxy)-benzofuran-2-carboxyliacid

To a stirred solution of methyl 5-(2-(2(S)-hydroxy-3-phenoxy-propylamino)-ethoxy)-benzofuran-2-carboxylic acid (0.10 g, 0.25 mmol) in methanol (5 mL) was added a solution of potassium hydroxide (42 mg, 0.75 mmol) in water (0.4 mL). After 15 hours, the reaction solution was concentrated in vacuo, the residue redissolved in water (4 mL) and the pH adjusted to between 5.0 and 5.5. The resulting solids were collected washed with water, diethyl ether and dried in vacuo to afford the title compound as an off-white solid. (78 mg; m.p. 128–133° C. Analytical Calculated for C$_{20}$H$_{21}$NO$_6$·1.25H$_2$O: C, 60.99; H, 6.02; N, 3.56. Found: C, 60.75; H, 5.86; N, 3.30).

Example 4

5-(2-(2(S)-Hydroxy-3-phenoxn-propylamino) ethoxy)-benzofuran-2-carboxalic acid, (2-methoxy-ethyl)-amide A solution of methyl 5-(2-(2(S)-hydroxy-3-phenoxy-propyl-amino)ethoxy)-benzofuran-2-carboxylic acid (0.10 g, 0.26 mmol) and 2-methoxyethyl-amine (0.6 mL) in methanol (3 mL) were maintained at reflux temperature for 18 h. The reaction solution was concentrated in vacuo and flash chromatographed on silica gel (5% methanol:chloroform) to afford the title compound as a colorless solid. (92 mg; m.p. 95–96° C. Analytical Calculated for C$_{23}$H$_{28}$N$_2$O$_6$·0.25H$_2$O: C, 63.79; H, 6.63; N, 6.47. Found: C, 63.59; H, 6.39; N, 6.34.)

Example 5

Isopropyl 5-(2-(2(S)-hydroxy-3-phenoxy-propylamino)ethoxy)-benzofuran-2-carboxylic acid Gaseous hydrogen chloride was slowly bubbled into a cooled (0° C.), stirred solution of methyl 5-(2-(2(S)-hydroxy-3-phenoxy-propylamino)ethoxy)-benzofuran-2-carboxylic acid (0.1 g, 0.25 mmol) in 2-propanol (5 ml) over a 5 minute period. The resulting solution was then refluxed for 16 hours, cooled and flash chromatographed (silica gel, 5% methanol:chloroform) to afford the title compound as a colorless solid. (0.09 g; m.p. 105–106° C. Analytical Calculated for $C_{23}H_{27}NO_6$: C, 66.09; H, 6.63; N, 3.35. Found: C, 66.04; H, 6.38; N, 3.31.)

Example 6

2-Bromo-1-(5-methoxy-benzofuran-2-yl)ethanone

To a cooled (0° C.), stirred solution of 5-methoxy-benzofuran-2-oyl chloride (prepared by treatment of 5-methoxy-benzofuran-2-carboxylic acid in refluxing thionyl chloride)(4.6 g, 22 mmol) in diethyl ether (20 ml) and dichloromethane (5 ml) was added a solution of diazomethane (66 mmol) in diethyl ether (45 ml). After 15 minutes gaseous hydrogen bromide was slowly bubbled in over a 20 minute period. After an additional 30 minutes, the reaction mixture was diluted with ethyl acetate, washed with saturated aqueous brine, the organic layer dried ($MgSO_4$) and concentrated in vacuo. The resultant red oil was flash chromatographed (silica gel,10% ethyl acetate:hexanes) to afford the title compound as a light-yellow colored solid. 2.8 g.

M.p. 86–87° C.

Example 7

Methyl 5-(2-(2(S)-hydroxy-3-(2-chlorophenoxy)-propylamino)ethoxy)-benzofuran-2-carboxylic acid The title compound was prepared by a procedure similar to that described in Example 1.

M.p. 126–126.5° C.

Analytical Calculated for $C_{21}H_{22}ClNO_6$: C, 60.07; H, 5.28; N, 3.34. Found: C, 59.89; H, 5.22 N, 3.25.

Example 8

Methyl 6-(2-(2(S)-hydroxy-3-phenoxy-propylamino) ethoxy)-benzofuran-2-carboxylic acid The title compound was prepared by a procedure similar to that described in Example 1.

M.p. 110–111° C.

Analytical Calculated for $C_{21}H_{23}NO_6$: C, 65.36; H, 5.86; N, 3.94. Found: C, 65.44; H, 6.02; N, 3.63.

Example 9

6-(2-(2(S)-Hydroxy-3-phenoxy-propylamino) ethoxy)-benzofuran-2-carboxic acid

The title compound was prepared by a procedure similar to that described in Example 1.

M.p. 214–217° C.

Analytical Calculated for $C_{20}H_{21}NO_6 \cdot 0.25H_2O$: C, 63.90; H, 5.76; N, 3.72. Found: C, 63.53; H, 5.66; N, 3.61.

Example 10

Methyl 5-(2-(2-(3-chloro-phenyl)-2(R)-hydroxy-ethylamino)-ethoxy)-benzofuran-2-carboxylic acid The title compound was prepared by a procedure similar to that described in Example 1.

M.p. 104–106° C.

Analytical Calculated for $C_{20}H_{20}ClNO_5$: C, 61.62; H, 5.17; N, 3.59. Found: C, 61.44; H, 4.96; N, 3.56.

Example 11

5-(2-(2-(3-Chloro-phenyl)-2(R)-hydroxy-ethylamino)-ethoxy)-benzofuran-2-carboxylic acid The title compound was prepared by a procedure similar to that described in Example 1.

M.p. 145–153° C.

Example 12

Methyl 6-(2-(2-(3-chloro-phenyl)-2(R)-hydroxy-ethylamino)-ethoxy)-benzofuran-2-carboxylic acid The title compound was prepared by a procedure similar to that described in Example 13

M.p. 102–103° C.

Analytical Calculated for $C_{20}H_{20}ClNO_5 \cdot 0.17H_2O$: C, 61.14; H, 5.22; N, 3.56. Found: C, 61.02; H, 5.39; N, 3.31.

Example 13

Methyl 5-(2-(2-(2-trifluoromethyl-thiazol-4-yl)-2(R)-hydroxy-ethylamino)-ethoxy)-benzofuran-2-caboxylic acid The title compound was prepared by a procedure similar to that described in Example 1.

M.p. 128–131° C.

Anal. Calcd for $C_{18}H_{17}F_3N_2O_5S$: C, 50.24; H, 3.98; N, 6.51. Found: C, 50.06; H, 3.87; N, 6.28.

Example 14

5-(2-(2-(2-Trifluoromethyl-thiazol-4-yl)-2(R)-hydroxy-ethylamino)-ethoxy)-benzofuran-2-carboxylic acid The title compound was prepared by a procedure similar to that described in Example 3.

M.p. 155–163° C. Analytical Calculated for $C_{17}H_{15}F_3N_2O_5S \cdot 2.25H_2O$: C, 44.7; H, 4.30; N, 6.13. Found: C, 44.45; H, 4.30; N, 6.13.

Example 15

1-(5-(2(2(S)-Hydroxy-3-phenoxy-propylamino)-ethoxy)-benzofuran-2-yl)-ethanone

The title compound was prepared by a procedure similar to that described in Example 1.

M.p. 122–123° C.

Analytical Calculated for $C_{21}H_{23}NO_5 \cdot 0.2H_2O$: C, 67.62; H, 6.32; N, 3.75. Found: C, 67.83; H, 6.10; N, 3.73.

Example 16

1-(5-(2(2(S)-Hydroxy-3-phenoxy-propylamino)-ethoxy)-benzofuran-2-yl)-butanone

The title compound was prepared by a procedure similar to that described in Example 1.

M.p. 99–100° C. Analytical Calculated for $C_{23}H_{27}NO_5 \cdot 0.14H_2O$: C, 69.05; H, 6.87; N, 3.50. Found: C, 69.08; H, 6.76; N, 3.34.

Example 17

1-(2-(2-Isoxazol-3-yl-benzofuran-6-yloxy)-ethylamino)-3phenoxy-propan-2(S)-ol

The title compound was prepared by a procedure similar to that described in Example 1.

M.p. 107–110° C. Analytical Calculated for $C_{22}H_{22}N_2O_5$: C, 66.99; H, 5.62; N, 7.10. Found: C, 66.94; H, 5.42; N, 7.00.

Example 18

1-(2-(2-Isoxazol-3-yl-benzofuran-5-yloxy)-ethylamino)-3-(2-chloro-phenoxy)-propan-2(S)-ol The title compound was prepared by a procedure similar to that described in Example 1.

M.p. 93–96° C.

Analytical Calculated for $C_{22}H_{21}ClN_2O_5 \cdot 0.25H_2O$: C, 60.97; H, 5.00; N, 6.46. Found: C, 60.99; H, 5.26; N, 5.60.

Example 19

1-(2-(2-(5-Methyl-isoxazol-3-yl)-benzofuran-5-yloxy)-ethylamino)-3-phenoxy-propan-2(S)-ol The title compound was prepared by a procedure similar to that described in Example 1.

M.p. 144–146° C. (acetone).

Analytical Calculated for $C_{23}H_{24}N_2O_5$: C, 67.63; H, 5.92; N, 6.86. Found: C, 67.65; H, 5.85; N, 6.73.

Example 20

1-(2-(2-(5-Methyl-isoxazol-3-yl)-benzofuran-5-yloxy)-ethylamino)-3-(2-chloro-phenoxy)-propan-2(S)-ol The title compound was prepared by a procedure similar to that described in Example 1.

M.p. 102–106° C.

Analytical Calculated for $C_{23}H_{23}ClN_2O_5$: C, 62.37; H, 5.23; N, 6.32. Found: C, 62.12; H, 5.58; N, 6.01.

Example 21

1-(2-(2-(5-Methyl-isoxazol-3-yl)-benzofuran-5-yloxy)-ethylamino)-3-(2-fluoro-phenoxy)-propan-2(S)-ol The title compound was prepared by a procedure similar to that described in Example 1.

M.p. 118–121° C.

Analytical Calculated for $C_{23}H_{23}FN_2O_5$: C, 64.78; H, 5.44; N, 6.57. Found: C, 64.97; H, 5.38; N, 6.22.

Example 22

1-(2-(2-Isoxazol-3-yl-benzofuran-5-yloxy)-ethylamino)-3-(2-trifluoromethyl-phenoxy)-propan-2(S)-ol The title compound was prepared by a procedure similar to that described in Example 1.

M.p. 90–91° C.

Analytical Calculated for $C_{23}H_{21}F_3N_2O_5$: C, 59.74; H, 4.58; N, 6.06. Found: C, 59.62; H, 4.49; N, 5.66.

Example 23

1-(2-(2-Isoxazol-3-yl-benzofuran-5-yloxy)-ethylamino)-3-(2-cyano-phenoxy)-propan-2(S)-ol The title compound was prepared by a procedure similar to that described in Example 1.

M.p. 94–95° C.

Analytical Calculated for $C_{23}H_{21}N_3O_5 \cdot 0.5H_2O$: C, 64.57; H, 5.18; N, 9.81. Found: C, 64.26; H, 5.16; N, 9.35.

Example 24

1-(2-(2-Isoxazol-3-yl-benzofuran-5-yloxy)-ethylamino)-3-(2-fluoro-phenoxy)-propan-2(S)-ol The title compound was prepared by a procedure similar to that described in Example 1.

M.p. 109–110° C.

Analytical Calculated for $C_{22}H_{21}FN_2O_5$: C, 64.07; H, 5.13; N, 6.79. Found: C, 63.89; H, 4.98; N, 6.39.

Example 25

1(R)-(3-Chloro-phenyl)-2-(2-(2-isoxazol-3-yl-benzofuran-5-yloxy)-5 ethylamino)-ethanol The title compound was prepared by a procedure similar to that described in Example 1.

M.p. 112–120° C.

Analytical Calculated for $C_{21}H_{19}ClN_2O_4$: C, 63.24; H, 4.57; N, 7.02. Found: C, 62.94; H, 5.13; N, 5.96.

Example 26

1(R)-(3-Trifluoromethyl-phenyl)-2-(2-(2-isoxazol-3-yl-benzofuran-5-yloxy)-ethylamino)-ethanol The title compound was prepared by a procedure similar to that described in Example 1.

M.p. 113–114° C.

Analytical Calculated for $C_{22}H_{19}F_3N_2O_4$: C, 61.11; H, 4.43; N, 6.48. Found: C, 61.48; H, 4.75; N, 5.79.

Example 27

1(R)-(3-Chloro-phenyl)-2-(2-(2-(5-methyl-isoxazol-3-yl)-benzofuran-5-yloxy)-ethylamino)-ethanol The title compound was prepared by a procedure similar to that described in Example 1.

M.p. 108–110° C.

Example 28

1(R)-(3-Trifluoromethyl-phenyl)-2-(2-(2-(5-methyl-isoxazol-3-yl)-benzofuran-5-yloxy)-ethylamino)-ethanol The title compound was prepared by a procedure similar to that described in Example 1.

M.p. 126–127° C.

Analytical Calculated for $C_{23}H_{21}F_3N_2O_4$: C, 61.88; H, 4.74; N, 6.27. Found: C, 61.75; H, 4.87; N, 6.20.

Example 29

1-(2-(2-(2-Methyl-thiazol-4-yl)-benzofuran-5-yloxy)-ethylamino)-3-phenoxy-propan-2(S)-ol;

The title compound was prepared by a procedure similar to that described in Example 1.

M.p. 150–152° C.

Example 30

1(R)-(3-Chloro-phenyl)-2-(2-(2-(2-methyl-thiazol-4-yl)-benzofuran-5-yloxy)-ethylamino)-ethanol The title compound was prepared by a procedure similar to that described in Example 1.

M.p. 127–129° C.

Analytical Calculated for $C_{22}H_{21}ClN_2O_3S$: C, 61.60; H, 4.93; N, 6.53. Found: C, 61.54; H, 4.85; N, 6.27.

Example 31

1-(2-(2-(5-Methyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 112–114° C.

Analytical Calculated for $C_{22}H_{23}N_3O_5$: C, 64.53; H, 5.66; N, 10.26. Found: C, 64.48; H, 5.24; N, 9.97.

Example 32

1-(2-(2-(5-Methyl-(1,2,4)-oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 106–108° C.

Anal. Calcd for $C_{22}H_{22}ClN_3O_5 \cdot 0.2H_2O$: C, 59.04; H, 5.04; N, 9.39. Found: C, 58.79; H, 4.93; N, 9.18.

Example 33

1-(2-(2-(5-Methyl-(1,2,4)-oxadiazol-3-yl)-benzofuran-5-yloxy)-ethylamino)-3-2-fluoro-phenoxy)-propan-2(S)-ol The title compound was prepared by a procedure similar to that described in Example 1.

M.p. 102.5–103.5° C.

Anal. Calcd for $C_{22}H_{22}FN_3O_5$: C, 61.82; H, 5.19; N, 9.83. Found: C, 61.60; H, 5.21; N, 9.52.

Example 34

1-(2-(2-(5-Trifluoromethyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 108–113° C.

Example 35

1-(2-(2-(5-Trifluoromethyl-(1,2,4)-oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 112–115° C.

Analytical Calculated for $C_{22}H_{19}F_3ClN_3O_5$: C, 53.08; H, 3.85; N, 8.44. Found: C, 53.65; H, 4.08; N, 8.36.

Example 36

1-(2-(2-(5-Trifluoromethyl-(1,2,4)-oxadiazol-3-yl)-benzofuran-5-yloxy)-ethylamino)-3-(2-fluoro-phenoxy)-propan-2(S)-ol The title compound was prepared by a procedure similar to that described in Example 1.

M.p. 117–119° C.

Analytical Calculated for $C_{22}H_{19}F_4N_3O_5$: C, 54.89; H, 3.98; N, 8.73. Found: C, 54.51; H, 3.84; N, 8.38.

Example 37

1-(2-(2-(5-Ethyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 97–98° C.

HRMS Calcd for $C_{23}H_{25}N_3O_5$: 423.1788. Found: 423.1843.

Example 38

1-(2-(2-(5-(2-Propyl)-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 111–112° C.

Analytical Calculated for $C_{24}H_{27}N_3O_5$: C, 65.89; H, 6.22; N, 9.60. Found: C, 15 65.61; H, 6.15; N, 9.24.

Example 39

1-(2-(2-(5-(2-Phenyl)-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 149–151 ° C.

Analytical Calculated for $C_{27}H_{25}N_3O_5$: C, 68.78; H, 5.34; N, 8.91. Found: C, 68.98; H, 5.29; N, 8.82.

Example 40

1-(2-(2-(5-(2-(3-Pyridyl))-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 150–155° C.

Example 41

1-(2-(2-(1,2,4)-Oxadiazol-3-yl)-benzofuran-5-yloxy)-ethylamino)-3-phenoxy-propan-2(S)-ol The title compound was prepared by a procedure similar to that described in Example 1.

M.p. 118–119° C.

Analytical Calculated for $C_{21}H_{21}N_3O_5$: C, 63.79; H, 5.35; N, 10.63. Found: C, 63.79; H, 5.34; N, 10.62. Found: C, 63.79; H, 5.35; N, 10.63.

Example 42

1-(2(2-(1,2,4)-Oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 102–104° C.

Analytical Calculated for $C_{21}H_{20}ClN_3O_5 \cdot 0.5H_2O$: C, 57.46; H, 4.82; N, 9.57. Found: C, 57.65; H, 4.71; N, 9.07.

Example 43

1-(2-(2-(1,2,4)-Oxadiazol-3-yl)-benzofuran-5-yloxy)-ethylamino)-3-(2-fluoro-phenoxy)-propan-2(S)-ol The title compound was prepared by a procedure similar to that described in Example 1.

M.p. 98–101° C.

Analytical Calculated for $C_{21}H_{20}FN_3O_5$: C, 61.01; H, 4.88; N, 10.16. Found: C, 61.39; H, 4.80; N, 9.01.

Example 44

1(R)-(3-Chloro-phenyl)-2-(2-(2-(5-methyl-(1,2,4)-oxadiazol-3-yl)-benzofuran-5-yloxy)-ethylamino)-ethanol The title compound was prepared by a procedure similar to that described in Example 1.

M.p. 88–92° C.

Analytical Calculated for $C_{21}H_{20}ClN_3O_4$: C, 60.94; H, 4.87; N, 10.15. Found: C, 60.95; H, 4.62; N, 9.75.

Example 45

1(R)-(3-Trifluoro-phenyl)-2-(2-(2-(5-methyl-(1,2,4)-oxadiazol-3-yl)-benzofuran-5-yloxy)-ethylamino)-ethanol The title compound was prepared by a procedure similar to that described in 5 Example 1.

M.p. 96–98° C.

Analytical Calculated for $C_{22}H_{20}F_3N_3O_4$: C, 59.06; H, 4.51; N, 9.39. Found: C, 58.78; H, 4.34; N, 9.17.

Example 46

1(R)-(2-Trifluoromethyl-thiazol-4-yl)-2-(2-(2-(5-methyl-(1,2,4)-oxadiazol-3-yl)-benzofuran-5-yloxy)-ethylamino)-ethanol The title compound was prepared by a procedure similar to that described in Example 1.

M.p. 143–146° C.

Analytical Calculated for $C_{19}H_{17}F_3N_4O_4S$: C, 50.22; H, 3.77; N, 12.33. Found: C, 50.77; H, 3.60; N, 11.67.

Example 47

1(R)-(3-Chloro-phenyl)-2-(2-(2-(5-trifluoromethyl-(1,2,4)-oxadiazol-3-yl)-benzofuran-5-yloxy)-ethylamino)-ethanol The title compound was prepared by a procedure similar to that described in Example 1.

M.p. 108–111° C.

Analytical Calculated for $C_{21}H_{17}F_3ClN_3O_4$: C, 53.92; H, 3.66; N, 8.98. Found: C, 53.93; H, 3.79; N, 8.75.

Example 48

1(R)-(3-Chloro-phenyl)-2-(2-(2-(5-(2-propyl)-(1,2,4)-oxadiazol-3-yl)-benzofuran-5-yloxy)-ethylamino)-ethanol The title compound was prepared by a procedure similar to that described in Example 1.

M.p. 84–87° C.

Analytical Calculated for $C_{23}H_{24}ClN_3O_4$: C, 62.51; H, 5.47; N, 9.51. Found: C, 62.34; H, 5.35; N, 9.34.

Example 49

1(R)-(3-Chloro-phenyl)-2-(2-(2-(1,2,4)-oxadiazol-3-yl-benzofuran-5-yloxy)-ethylamino)-ethanol The title compound was prepared by a procedure similar to that described in Example 1.

M.p. 103–105° C.

Analytical Calculated for $C_{20}H_{18}ClN_3O_4$: C, 60.08; H, 4.54; N, 10.51. Found: C, 60.19; H, 4.42; N, 9.58.

Example 50

5-(2-(2(S)-Hydroxy-3-phenoxn-propylamino)ethoxy)-benzofuran-2-carboxylic acid, 1-propyl-amide The title compound was prepared by a procedure similar to that described in Example 4.

M.p. 127–128° C.

Example 51

(5-(2-(2(S)-Hydroxy-3-phenoxy-propylamino)ethoxy)-benzofuran-2-yl)-pyrrolidin-1-yl-methanone The title compound was prepared by a procedure similar to that described in Example 4.

M.p. 117–118° C.

Analytical Calculated for $C_{24}H_{28}N_2O_5 \cdot 0.2H_2O$: C, 67.34; H, 6.69; N, 6.54. Found: C, 67.11; H, 6.24; N, 6.40.

Example 52

(5-(2-(2(S)-Hydroxy-3-(2-chloro-phenoxy)-propylamino)ethoxy)-benzofuran-2-yl)-pyrrolidin-1-yl-methanone The title compound was prepared by a procedure similar to that described in Example 4.

M.p. 89–90° C.

Analytical Calculated for $C_{24}H_{27}ClN_2O_5$: C, 62.80; H, 5.93; N, 6.11. Found: C, 30 62.59; H, 5.80; N, 5.94.

Example 53

(5-(2-(2 (S)-Hydroxy-3-phenoxy-propylamino)ethoxy)-indol-2-yl)-pyrrolidin-1-yl-methanone The title compound was prepared by a procedure similar to that described in Example 4.

M.p. 110–115° C.

Example 54

(1-Methyl-5-(2-(2(S)-hydroxy-3-phenoxy-propylamino)ethoxy)-indol-2-yl)-pyrrolidin-1-yl-methanone The title compound was prepared by a procedure similar to that described in Example 4.

M.p. 130–131° C.

Analytical Calculated for $C_{25}H_{31}N_3O_4 \cdot 0.5H_2O$: C, 67.23; H, 7.22; N, 9.41.

Found: C, 67.55; H, 6.98; N, 9.15.

Example 55

5-(2-(2-(3-Chloro-phenyl)-2(R)-hydroxy-ethylamino)-ethoxy)-benzofuran-pyrrolidin-1-yl-methanone The title compound was prepared by a procedure similar to that described in Example 4.

M.p. 96–98° C.

Analytical Calculated for $C_{23}H_{25}ClN_2O_4$: C, 64.41; H, 5.88; N, 6.53. Found: C, 64.41; H, 5.73; N, 6.19.

Example 56

5-(2(R,S)-(2-(2-Trifluoromethyl-thiazol-4-yl)-2(S)-hydroxy-ethylamino)-propl)-benzofuran-2-carboxylic acid The title compound was prepared by a procedure similar to that described in Example 3.

M.p. 145–163° C.

Analytical Calculated for $C_{18}H_{17}F_3N_2O_4S \cdot 1.25H_2O$: C, 49.48; H, 4.50; N, 6.41. Found: C, 49.38; H, 4.56; N, 6.23.

Example 57

5-(2(R)-(2-(2-Trifluoromethyl-thiazol-4-yl)-2(S)-hydroxy-ethylamino)-propyl)-benzofuran-2-carboxylic acid The title compound was prepared by a procedure similar to that described in Example 3.

M.p. 168–171 ° C.

Analytical Calculated for $C_{18}H_{17}F_3N_2O_4S \cdot 1.5H_2O$: C, 48.98; H, 4.57; N, 6.35. Found: C, 49.04; H, 4.47; N, 6.06.

Example 58

4-(2(R,S)-(2-(2-Trifluoromethyl-thiazol-4-yl)-2(S)-hydroxy-ethylamino)-propyl)-benzo-furan-2-carboxylic acid The title compound was prepared by a procedure similar to that described in Example 3.

M.p. 158–176° C.

Analytical Calculated for $C_{18}H_{17}F_3N_2O_4S \cdot 1.25H_2O$: C, 48.98; H, 4.57; N, 6.35. Found: C, 48.87; H, 4.31; N, 6.27.

Example 59

5-(2(R,S)-(2-(3-Chloro-phenyl)-2(R)-hydroxy-ethylamino)-propyl)-1H-indole-2-carboxylic acid ethyl ester The title compound was prepared by a procedure similar to that described in Example 1.

M.p. 43–44° C.

Example 60

5-(2(R,S)-(2-(3-Chloro-phenyl)-2(R)-hydroxy-ethylamino)-propyl)-1H-indole-2-carboxylic acid The title compound was prepared by a procedure similar to that described in Example 3.

M.p. 160–165° C.

Example 61

5-(2(R,S)-(2(S)-Hydroxy-3-phenoxy-propylamino)-propyl)-1H-indole-2-carboxylic acid The title compound was prepared by a procedure similar to that described in Example 3.

M.p. 127–129° C.

Example 62

5-(2(R,S)-(2-(3-Chloro-phenyl)-2(R)-hydroxy-ethylamino)-propyl)-1-methyl-1H-indole-2-carboxylic acid ethyl ester The title compound was prepared by a procedure similar to that described in Example 1.

M.p. <30° C.

Analytical Calculated for $C_{23}H_{27}ClN_2O_3 \cdot 1.5H_2O$: C, 62.51; H, 6.84; N, 6.34. Found: C, 62.51; H, 6.46; N, 5.83.

Example 63

5-(2(R,S)-(2-(3-Chloro-phenyl)-2(R)-hydroxy-ethylamino)-propyl)-1-methyl-1H-indole-2-carboxylic acid The title compound was prepared by a procedure similar to that described in Example 3.

M.p. 142–146° C.

Example 64

5-(2(R,S)-(2(S)-Hydroxy-3-phenoxy-propylamino)-propyl)-1-methyl-1H-indole-2-carboxylic acid The title compound was prepared by a procedure similar to that described in Example 3.

M.p. 98–100° C.

Example 65

5-(2(R)-(2-(3-Chloro-phenyl)-2(R)-hydroxy-ethylamino)-propyl)-1-cyclopropylmethyl-1H-indole-2-carboxylic acid methyl ester The title compound was prepared by a procedure similar to that described in Example 2.

M.p. 135–137° C.

Analytical Calculated for $C_{25}H_{29}ClN_2O_3$: C, 62.89; H, 6.33; N, 5.87. Found: C, 62.51; H, 6.53; N, 5.79.

Example 66

5-(2(R)-(2-(3-Chloro-phenyl)-2(R)-hydroxy-ethylamino)-propyl)-1-cyclopropylmethyl-1H-indole-2-carboxylic acid The title compound was prepared by a procedure similar to that described in Example 3.

M.p. 207–209° C.

Example 67

1-Benzyl-5-(2(R)-(2-(3-chloro-phenyl)-2(R)-hydroxy-ethylamino)-propyl)-1H-indole-2-carboxylic acid methyl ester, hydrochloride salt.

The title compound was prepared by a procedure similar to that described in Example 2.

M.p. 201–203° C.

Analytical Calculated for $C_{28}H_{30}Cl_2N_2O_3$: C, 65.50; H, 5.89; N, 5.46. Found: C, 65.66; H, 6.00; N, 4.90.

Example 68

1-Benzyl-5-(2(R)-(2-(3-chloro-phenyl)-2(R)-hydroxy-ethylamino)-propyl)-1H-indole-2-carboxylic acid The title compound was prepared by a procedure similar to that described in Example 3.

M.p. 128–130° C.

Example 69

1-Benzyl-5-(2(R S)-(2(S)-hydroxy-3-phenoxy-propylamino)-propl)-1H-indole-2-carboxylic acid ethyl ester The title compound was prepared by a procedure similar to that described in Example 1.
M.p. 168–174° C.
Analytical Calculated for $C_{30}H_{35}ClN_2O_4$: C, 68.89; H, 6.74; N, 5.36. Found: C, 68.78; H, 6.91; N, 5.01.

Example 70

1-Benzyl-5-(2(R,S)-(2S)-hydroxy-3-phenoxy-propylamino)-propyl)-1H-indole-2-carboxylic acid The title compound was prepared by a procedure similar to that described in Example 3.
M.p. 170–181° C.
Analytical Calculated for $C_{26}H_{30}N_2O_4 \cdot 1.25H_2O$: C, 69.91; H, 6.81; N, 5.82. Found: C, 69.71; H, 6.44; N, 5.13.

Example 71

1-(3-Carboxy-benzyl)-5-(2(R)-(2-(3-chloro-phenyl)-2(R)-hydroxy-ethylamino)-propyl)-1H-indole-2-carboxylic acid, potassium salt.

The title compound was prepared by a procedure similar to that described in Example 3.
M.p. 237–240° C.

Example 72

1-(3-Carboxy-benzyl)-5-(2(R,S)-(2(S)-hydroxy-3-phenoxy-propylamino)-propyl)-1H- indole-2-carboxylic acid, potassium salt The title compound was prepared by a procedure similar to that described in Example 3.
M.p. 110–115° C.

Example 73

1-(4-Carboxy-benzyl)-5-(2(R)-(2-(3-chloro-phenyl)-2(R)-hydroxy-ethlamino)-propyl)-1H-indole-2-carboxylic acid, potassium salt The title compound was prepared by a procedure similar to that described in Example 3.
M.p. 223–225° C.

Example 74

5-(2(R,S)-(2-(3-Chloro-phenyl)-2(R)-hydroxy-ethylamino)-propyl)-1-(4-dimethylsulfamoyl-benzyl)-1H-indole-2-carboxylic acid ethyl ester The title compound was prepared by a procedure similar to that described in Example 1.
M.p. 122–124° C.
Analytical Calculated for $C_{31}H_{36}ClN_3O_5S \cdot 0.25H_2O$: C, 61.77; H, 6.10; N, 6.97. Found: C, 61.66; H, 6.07; N, 6.38.

Example 75

5-(2-(R,S)(2-(3-Chloro-phenyl)-2(R)-hydroxy-ethylamino)-propyl)-1-(4-dimethylsulfamoyl-benzyl)-1H-indole-2-carboxylic acid The title compound was prepared by a procedure similar to that described in Example 3.

M.p. 168–175° C.

Example 76

1-(4Dimethylsulfamoyl-benzyl)-5-(2(R,S)-(2(S)-hydroxy-3-phenoxy-propylamino)-propyl)-1H-indole-2-carboxylic acid ethyl ester The title compound was prepared by a procedure similar to that described in Example 1.
M.p. 112–114° C.
Analytical Calculated for $C_{32}H_{39}N_3O_6S \cdot 0.5H_2O$: C, 63.76; H, 6.69; N, 6.97. Found: C, 63.99; H, 6.58; N, 6.44.

Example 77

1-(4-Dimethylsulfamoyl-benzyl)-5-(2(R,S)-(2(S)-hydroxy-3-phenoxy-propylamino)-propyl)-1H-indole-2-carboxylic acid The title compound was prepared by a procedure similar to that described in Example 3.
M.p. 148–156° C.
Analytical Calculated for $C_{30}H_{35}N_3O_6S \cdot 2.5H_2O$: C, 58.99; H, 6.60; N, 6.88. Found: 58.76; H, 6.20; N, 6.44.

Example 78

5-(2(R,S)-(2-(3-Chloro-phenyl)-2(R)-hydroxy-ethylamino)-propyl)-1-(4-methanesulfonylamino-benzyl)-1H-indole-2-carboxylic acid ethyl ester, hydrochloride salt The title compound was prepared by a procedure similar to that described in Example 1.
M.p. >200° C.
Analytical Calculated for $C_{30}H_{35}Cl_2N_3O_5S \cdot 0.6H_2O$:C, 57.06; H, 5.77; N, 6.65. Found: C, 57.03; N, 6.00; N, 6.33.

Example 79

5-(2(R,S)-(2-(3-Chloro-phenyl)-2(R)-hydroxy-ethylamino)-propyl)-1-(4-methanesulfonylamino-benzyl)-1H-indole-2-carboxylic acid The title compound was prepared by a procedure similar to that described in Example 3.
M.p. >200° C.
Analytical Calculated for $C_{28}H_{30}Cl_2N_3O_5S \cdot 3H_2O$: C, 55.11; H, 5.94; N, 6.88. Found: C, 54.96; H, 5.41; N, 6.56.

Example 80

5-(2(R,S)-(2(S)-Hydroxy-3-phenoxy-propylamino)-propyl)-1-(4-methanesulfonylamino-benzyl)-1H-indole-2-carboxylic acid ethyl ester, hydrochloride salt The title compound was prepared by a procedure similar to that described in Example 1.
M.p. 61–65° C.
Analytical Calculated for $C_{31}H_{38}ClN_3O_6S$: C, 60.43; H, 6.22; N, 6.82. Found: C, 60.53; H, 6.22; N, 6.65.

Example 81

5-(2(R,S)-(2(S)-Hydroxy-3-phenoxy-propylamino)-propyl)-1-(4-methanesulfonylamino-benzyl)-1H-indole-2-carboxylic acid The title compound was prepared by a procedure similar to that described in Example 3.

M.p. 180–190° C.

Analytical Calculated for $C_{29}H_{33}N_3O_6S \cdot 1.75H_2O$: C, 59.68; H, 6.00; N, 7.20. Found: C, 59.77; H, 6.02; N, 7.08.

Example 82

1-(3-Carbamoyl-benzyl)-5-(2(R,S)-(2-(3-chloro-phenyl)-2(R)-hydroxyethylamino)-propyl)-1H-indole-2-carboxylic acid, potassium salt The title compound was prepared by a procedure similar to that described in Example 3.

M.p. 168–172° C.

Example 83

1-(3-Carbamoyl-benzyl)-5-(2(R,S)-(2(S)-hydroxy-3-phenoxy-propylamino)-propyl)-1H-indole-2-carboxylic acid ethyl ester, hydrochloride salt The title compound was prepared by a procedure similar to that described in Example 1.

M.p. 125–128° C.

Analytical Calculated for $C_{31}H_{36}ClN_3O_5 \cdot 1H_2O$: C, 63.74; H, 6.55; N, 7.19. Found: C, 63.84; N, 6.55; N, 7.29.

Example 84

1-(3-Carbamoyl-benzyl)-5-(2-(R,S)(2(S)-hydroxy-3-phenoxy-propylamino)-propyl)-1H-indole-2-carboxylic acid, potassium salt The title compound was prepared by a procedure similar to that described in Example 3.

M.p. 160–164° C.

Analytical Calculated for $C_{29}H_{30}N_3O_5K \cdot 2.5H_2O$: C, 59.57; H 6.03; N, 7.19. Found: C, 59.31; H, 5.44; N, 7.23.

Example 85

5(2(R,S)-(2-(3-Chloro-phenyl)-2(R)-hydroxy-ethylamino)-propyl)-1-(3-(dimethoxy-phosphoryl)-benzyl)-1H-indole-2-carboxylic acid ethyl ester, hydrochloride salt The title compound was prepared by a procedure similar to that described in Example 1.

M.p. 110–148° C.

Analytical Calculated for $C_{31}H_{37}Cl_2N_2O_6PS$: C, 58.59; H, 5.87; N, 4.41. Found: C, 58.25; H, 6.23; N, 3.98.

Example 86

5(2(R,S)-(2-(3-Chloro-phenyl)-2(R)-hydroxy-ethylamino)-propyl)-1-(3-(dimethoxy-phosphoryl)-benzyl)-1H-indole-2-carboxylic acid The title compound was prepared by a procedure similar to that described in Example 3.

M.p. >200° C.

Example 87

5-(2(R,S)-(2-(3-Chloro-phenyl)-2(R)-hydroxy-ethylamino)-propyl)-1-(3-phosphono-benzyl)-benzyl)-1H-indole-2-carboxylic acid, hydrobromide salt The title compound was prepared by a procedure similar to that described in Example 3.

M.p. >200° C.

Analytical Calculated for $C_{27}H_{28}BrClN_2O_6P \cdot 2.5H_2O$: C, 48.47; H, 4.97; N, 4.19. Found: C, 48.27; H, 5.17; N, 4.22.

Example 88

5-(2(R,S)-(2-(3-Chloro-phenyl)-2(R)-hydroxy-ethylamino)-propyl)-1-(4-(dimethoxy-phosphoryl)-benzyl)-1H-indole-2-carboxylic acid ethyl ester, hydrochloride salt The title compound was prepared by a procedure similar to that described in Example 1.

M.p. 90–105° C.

Example 89

5-(2(R,S)-(2-(3-Chloro-phenyl)-2(R)-hydroxy-ethylamino)-propyl)-1-(4-(dimethoxy-phosphoryl)-benzyl)-1H-indole-2-carboxylic acid The title compound was prepared by a procedure similar to that described in Example 3.

M.p. 218–220° C.

Analytical Calculated for $C_{29}H_{32}N_2O_6P \cdot 2.5H_2O$: C, 56.50; H, 5.23; N, 4.54. Found: C, 56.15; H, 5.39; N, 4.65.

Example 90

5-(2(R,S)-(2-(3-Chloro-phenyl)-2(R)-hydroxy-ethylamino)-propyl)-1-(4phosphono-benzyl)-benzyl)-1H-indole-2-carboxylic acid The title compound was prepared by a procedure similar to that described in Example 3.

M.p. >200° C.

Example 91

30 1-(3-Dimethoxy-phosphoryl)-benzyl)-5-(2(R,S)-(2(S)-hydroxy-3-phenoxy- propylamino)-propyl)-1H-indole-2-carboxylic acid ethyl ester, hydrochloride salt The title compound was prepared by a procedure similar to that described in Example 1.

M.p. 118–132° C.

Analytical Calculated for $C_{32}H_{39}N_2O_7P \cdot 0.5H_2O$: C, 60.04; H, 6.29; N, 4.38. Found: C, 60.17; H, 6.64; N, 4.45.

Example 92

1-(3-Dimethoxy-phosphoryl)-benzyl)-5-(2(R,S)-(2(S)-hydroxy-3-phenoxy-propylamino)-propyl)-1H-indole-2-carboxylic acid The title compound was prepared by a procedure similar to that described in Example 3.

M.p. 173–180° C.

Analytical Calculated for $CH_{35}N_2O_7P \cdot 1.3H_2O$: C, 61.00; H, 6.37; N, 4.74. Found: C, 61.05; H, 6.40; N, 4.90.

Example 93

5-(2(R,S)-(2(S)-Hydroxy-3-phenoxy-propylamino)-propyl)-1-(3-phosphono-benzyl)-1H-indole-2-carboxylic acid The title compound was prepared by a procedure similar to that described in Example 3.

M.p. >200° C.

Analytical Calculated for $C_{28}H_{32}BrN_2O_7P \cdot 3.2H_2O$: C, 49.66; H, 5.57; N, 4.14. Found: C, 49.42; H, 5.62; N, 4.66.

Example 94

1-(4-Dimethoxy-phosphoryl)-benzyl)-5-(2(R,S)-(2(S)-hydroxy-3-phenoxy-propylamino)-propyl)-1H-indole-2-carboxylic acid ethyl ester, hydrochloride salt The title compound was prepared by a procedure similar to that described in Example 1.

M.p. 75–85° C.

Example 95

1-(4-Dimethoxy-phosphoryl)-benzyl-5-(2(R,S)-(2(S)-hydroxy-3-phenoxy-propylamino)- propyl)-1H-indole-2-carboxylic acid The title compound was prepared by a procedure similar to that described in Example 3.

M.p. 188–192° C.

Analytical Calculated for $C_{30}H_{35}N_2O_7P \cdot 1H_2O$: C, 61.63; H, 6.37; N, 4.79. Found: C, 61.24; H, 6.37; N, 4.87.

Example 96

5-(2(R,S)-(2(S)-Hydroxy-3-phenoxy-propylamino)-propyl)-1-(4-phosphono-benzyl)-1H-indole-2-carboxylic acid, hydrobromide salt The title compound was prepared by a procedure similar to that described in Example 1.

M.p. 130–135° C.

Example 97

5-(2(R,S)-(2-(3-Chloro-phenyl)-2(R)-hydroxy-ethylamino)-propyl)-1-(3-dimethylcarbamoyl-benzyl)-1H-indole-2-carboxylic acid ethyl ester, hydrochloride salt The title compound was prepared by a procedure similar to that described in Example 3.

M.p. 94–96° C.

Analytical Calculated for $C_{32}H_{37}Cl_2N_3O_4 \cdot 0.5H_2O$: C, 63.26; H, 6.30; N, 6.91. Found: C, 62.87; H, 6.26; N, 6.74.

Example 98

5-(2(R,S)-(2-(3-Chloro-phenyl)-2(R)-hydroxy-ethylamino)-propyl)-1-(3-dimethylcarbamoyl-benzyl)-1H-indole-2-carboxylic acid, potassium salt The title compound was prepared by a procedure similar to that described in Example 3.

M.p. 72–75° C.

Analytical Calculated for $C_{30}H_{31}ClN_3O_4K \cdot 3H_2O$: C, 57.54; H, 5.96; N, 6.71. Found: C, 57.24; H, 5.66; N, 6.57.

Example 99

1-(4-Dimethylcarbamoyl-benzyl)-5-(2(R,S)-(2(S)-hydroxy-3-phenoxy-propylamino)-propyl)-1H-indole-2-carboxylic acid The title compound was prepared by a procedure similar to that described in Example 3.

M.p. 94–97° C.

Analytical Calculated for $C_{31}H_{34}N_3O_5 \cdot 2.5H_2O$: C, 60.76; H, 6.42; N, 6.86. Found: C, 30 60.61; H, 5.84; N, 6.73.

Example 100

5-(2(R)-(2-(3-Chloro-phenyl)-2(R)-hydroxy-ethylamino)-propyl)-1-pyridin-4-ylmethyl-1H-indole-2-carboxylic acid methyl ester, hydrochloride salt The title compound was prepared by a procedure similar to that described in Example 2.

M.p. 85–88° C.

Example 101

5-(2(R)-(2-(3-Chloro-phenyl)-2(R)-hydroxy-ethylamino)-propyl)-1-pyridin-4-ylmethyl-1H-indole-2-carboxylic acid, potassium salt The title compound was prepared by a procedure similar to that described in Example 3.

M.p. 188–190° C.

Example 102

5-(2(R,S)-(2-(3-Chloro-phenyl)-2(R)-hydroxy-ethylamino)-propyl)-1-pyrimidin-4-ylmethyl-1H-indole-2-carboxylic acid The title compound was prepared by a procedure similar to that described in Example 3.

M.p. 158–161° C.

Analytical Calculated for $C_{25}H_{25}ClN_4O_3 \cdot 1H_2O$: C, 61.21; H, 5.78; N, 11.90. Found: C, 20 61.39; H, 5.71; N, 10.76.

Example 103

5-(2(R,S)-(2-(3-Chloro-phenyl)-2(R)-hydroxy-ethylamino)-propyl)-1-(4-methanesulfonyl-benzyl)-1H-indole-2-carboxylic acid methyl ester, hydrochloride salt The title compound was prepared by a procedure similar to that described in Example 1.

M.p. 196–197° C.

Analytical Calculated for $C_{29}H_{31}ClN_2O_5S$: C, 58.88; H, 5.45; N, 4.74. Found: C, 58.56; H, 5.43; N, 4.44.

Example 104

5-(2( R, S)-(2-(3-Chloro-phenyl)-2(R)-hydroxy-ethylamino)-propyl)-1-(4-methanesulfonyl-benzyl)-1H-indole-2-carboxylic acid The title compound was prepared by a procedure similar to that described in Example 3.

M.p. 150–155° C.

Example 105

1-Benzyl-(5-(2(R,S)-(2-(3-chloro-phenyl)-2(R)-hydroxy-ethylamino)-propyl)-1H-indol-2-yl)-acetic acid methyl ester hydrochloride salt The title compound was prepared by a procedure similar to that described in Example 1.

M.p. 137–142° C.

Analytical Calculated for $C_{29}H_{32}Cl_2N_2O_3 \cdot 0.25H_2O$: C, 65.46; H, 6.11; N, 5.27. Found: C, 65.58; H, 6.11; N, 5.18.

Example 106

1-Benzyl-(5-(2(R,S)-(2-(3-chloro-phenyl)-2(R)-hydroxy-ethylamino)-propyl)-1H-indol-2-yl)-acetic acid The title compound was prepared by a procedure similar to that described in Example 3.

M.p. 131–141° C.

Analytical Calculated for $C_{28}H_{29}ClN_2O_3 \cdot 1.25H_2O$: C, 67.35; H, 6.10; N, 5.61. Found: C, 67.35; H, 6.29; N, 5.56.

Example 107

1-Benzyl-(5-(2(R,S)-(2(S)-hydroxy-3-phenoxy-propylamino)-propyl)-1H-indol-2-yl)-acetic acid methyl ester, hydrochloride salt The title compound was prepared by a procedure similar to that described in Example 1.

M.p. 162–175° C.

Analytical Calculated for $C_{30}H_{34}N_2O_4 \cdot 1H_2O$: C, 66.59; H, 6.71; N, 5.18. Found: C, 66.44; H, 6.81; N, 5.21.

Example 108

1-Benzyl-(5-(2(R,S)-(2(S)-hydroxy-3-phenoxy-propylamino)-propyl)-1H-indol-2-yl)-acetic acid The title compound was prepared by a procedure similar to that described in Example 3.

M.p. 153–158° C.

Analytical Calculated for $C_{29}H_{32}N_2O_4 \cdot 0.6H_2O$: C, 72.04; H, 6.92; N, 5.79. Found: C, 72.35; H, 7.00; N, 5.65.

Example 109

1-[2-(2-[1,2,4]Oxadiazol-3-yl-benzo[b]thiophen-5-yloxy)-ethylamino]-3-phenoxy-propan-2(S)-ol The title compound was prepared by a procedure similar to that described in Example 1.

M.p. 101–102° C.

Analytical Calculated for $C_{21}H_{21}N_3O_4S$: C, 61.30; H, 5.14; N 10.21. Found: C, 60.78; H, 4.80; N, 9.61. 1 H NMR (CDCl$_3$): d=8.74 (s, 1 H); 7.98 (s, 1 H); 7.72 (d, 1 H); 7.26 (m, 3 H); 7.08 (d, 1 H); 6.91 (m, 3 H); 4.15 (m, 2 H); 4.08 (m, 1 H); 4.00 (m, 2 H); 3.09 (m, 2 H); 2.95 (m, 1 H); 2.87 (m, 1 H); 2.16 (br, 2 H, NH and OH). MS (NH$_3$ Cl): m/e=412 (M+H+, 80%); 369 (M+H+—HNCO, 100%).

Example 110

5-[2-(2(S)-Hydroxy-3-phenoxy-propylamino)-ethoxy]-benzo[b]thiophene-2-carboxylic acid The title compound was prepared by a procedure similar to that described in Example 3.

M.p. 261–262° C. 1H NMR (DMSO-d6): d=7.75 (d, 1 H); 7.60 (s, 1 H); 7.41 (m, 1 H); 7.29 (m, 2 H); 7.02 (d, 1 H); 6.96 (m, 3 H); 4.28 (m, 1 H); 4.25 (m, 2 H); 3.98 (m, 2 H); 3.35 (m, 2 H); 3.21 (m, 1H); 3.17 (m, 1H). MS (FAB CH$_4$ Cl): m/e=388 (M+H+, 80%).

Example 111

5-[2-(2(S)-Hydroxy-3-phenoxy-propylamino)-ethoxy]-benzo[b]thiophene-2-carboxylic acid ethyl ester The title compound was prepared by a procedure similar to that described in Example 1.

M.p. 99–100° C. 1H NMR (CDCl$_3$): d=7.93 (s, 1 H); 7.68 (d, 1 H); 7.24 (m, 3 H); 7.07 (d, 1 H); 6.90 (m, 3 H); 4.38 (q, 2 H); 4.12 (m, 3 H); 3.98 (m, 2 H); 3.08 (m, 2 H); 2.94 (m, 1 H); 2.86 (m, 1 H), 2.44 (br, 2 H, NH and OH). MS (NH$_3$ Cl): m/e=416 (M+H+, 100%).

Example 112

1-[2-(2-[1,2,4]Oxadiazol-3-yl-benzothiazol-6-yloxy)-ethylamino]-3-Phenoxy-propan-2(S)-ol The title compound was prepared by a procedure similar to that described in Example 1.

M.p. viscous oil at 25° C. 1H NMR (CDCl$_3$): d=8.87 (s, 1 H); 8.10 (d, 1 H); 7.38 (d, 1 H); 7.23 (m, 2 H); 7.15 (d, 1 H); 6.91 (m, 3 H); 4.16 (m, 2 H); 4.08 (m, 1H); 4.02 (m, 2 H); 3.11 (m, 2 H); 2.96 (d of d, 1 H); 2.86 (d of d, 1 H). MS (FAB CH$_4$ Cl): m/e=413 (M+H+, 100%).

Example 113

1-Phenoxy-3-{2-[2-(1H-tetrazol-5-yl)-benzothiazol-6-yloxy]-ethylamino}-propan-2(S)-ol The title compound was prepared by a procedure similar to that described in Example 1.

M.p. viscous oil at 25° C. 1H NMR (DMSO-d6): d=7.92 (d, 1 H); 7.73 (d, 1 H); 7.30 (m, 2 H); 7.16 (d, 1 H); 6.96 (m, 3 H); 4.40 (m, 2 H); 4.21 (m, 1 H); 4.03 (m, 2 H); 3.54 (m, 2 H); 3.38 (m, 2 H). MS (FAB CH$_4$ Cl): m/e=413 (M+H+, 50%).

Example 114

1-Benzyl-5-(2(R,S)-(2(R,S)-hydroxy-2-tetrazolo(1,5-a)pyridine-6-yl-ethylamino)-propyl)-1H-indole-2-carboxylic acid ethyl ester dihydrochloride salt The title compound was prepared by a procedure similar to that described in Example 2.

M.p. 110–115° C.

Example 115

1-Benzyl-5-(2(R,S)-(2(R,S)-hydroxy-2-tetrazolo(1,5-a)pyridine-6-yl-ethylamino)-propyl)-1H-indole-2-carboxylic acid The title compound was prepared by a procedure similar to that described in Example 3.

M.p. 201–205° C.

Analytical calculated for $C_{26}H_{26}N_6O \cdot 2.25H_2O$: C, 61.11; H, 6.02; N, 16.44. Found C, 61.01; H, 5.66; N, 16.70.

Example 116

5-(2(R,S)-(2(R,S)-(6-Amino-pyridin-3-yl)-2-hydroxy-ethylamino)-propyl)-1-benzyl-1H-indole-2-carboxylic acid ethyl ester The title compound was prepared by a procedure similar to that described in Example 2.

M.p. 58–66° C.

Analytical calculated for $C_{28}H_{32}N_4O_3 \cdot 0.25H_2O$: C, 70.49; H, 6.87; N, 11.74. Found: C, 70.37; H, 6.94; N, 11.74.

Example 117

5-(2(R,S)-(2(R,S)-(6-Amino-pyridin-3-yl)-2-hydroxy-ethylamino)-propyl)-1-benzyl-1H-indole-2-carboxylic acid hydrochloride salt The title compound was prepared by a procedure similar to that described in Example 3.

M.p. 58–66° C.

Analytical calculated for $C_{26}H_{28}N_4O_3 \cdot HCl \cdot 1.0H_2O$: C, 62.58; H, 6.26; N, 11.23. Found: C, 62.41; H, 6.25; N, 11.13

Example 118

5-(2(R,S)-(2(R)-Hydroxy-3-phenoxy-propylamino)-propyl)-1-(2-methanesulfonylamino-benzyl)-1H-indole-2-carboxylic acid The title compound was prepared by a procedure similar to that described in Example 3.

M.p. 140–150° C.

We claim:

1. A compound of the formula

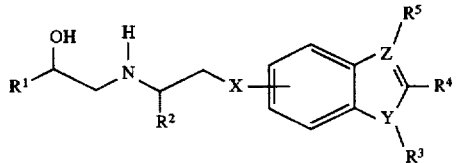

wherein $R^1$ is phenyl, —$(CH_2)_n$—O-phenyl, pyridyl, pyrimidyl or thiazolyl; wherein said phenyl and the phenyl moiety of said —$(CH_2)_n$—O-phenyl may optionally be substituted with one or more substituents independently selected from hydrogen, ($C_1$–$C_6$)alkyl optionally substituted with one or more halo atoms, hydroxy, ($C_1$–$C_6$)alkoxy optionally substituted with one or more halo atoms, ($C_1$–$C_6$)alkylthio, fluoro, chloro, bromo, iodo, nitro, amino, —$NR^7R^8$ and cyano; and wherein each of the ring carbon atoms of said pyridyl, pyrimidinyl or thiazolyl may optionally be substituted with a substituent independently selected from hydrogen, ($C_1$–$C_6$)alkyl optionally substituted with one or more halo atoms, hydroxy, ($C_1$–$C_6$)alkoxy optionally substituted with one or more halo atoms, ($C_1$–$C_6$)alkylthio, fluoro, chloro, bromo, iodo, nitro, amino, —$NR^7R^8$ and cyano;

$R^2$ is hydrogen or ($C_1$–$C_6$)alkyl optionally substituted with one or more halo atoms;

$R^3$ is hydrogen, —$(CH_2)_n$-phenyl —$(C_1$–$C_{10})$alkyl, —$(CH_2)_n$—$NR^7R^8$, —$(CH_2)_n$—$CO_2R^2_1$,

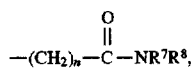

—$(CH_2)_n$—$OR^2$, —$(CH_2)_n$—$SO_3R^2$, —$(CH_2)_n$—$SO_2$—($C_1$–$C_6$)alkyl, —$(CH_2)_n$—$SO_2NR^7R^8$, or a heterocycle selected from —$(CH_2)_n$-pyridyl, —$(CH_2)_n$-pyrimidyl, —$(CH_2)_n$-pyrazinyl, —$(CH_2)_n$-isoxazolyl, —$(CH_2)_n$-oxazolyl, —$(CH_2)_n$-thiazolyl, —$(CH_2)_n$-(1,2,4-oxadiazolyl), —$(CH_2)_n$-imidazolyl, —$(CH_2)_n$-triazolyl and —$(CH_2)_n$-tetrazolyl; wherein one of the ring nitrogen atoms of said —$(CH_2)_n$-imidazolyl, —$(CH_2)_n$-triazolyl and —$(CH_2)_n$-tetrazolyl may optionally be substituted by ($C_1$–$C_6$)alkyl optionally substituted with one or more halo atoms; wherein each of said heterocycles may optionally be substituted on one or more of the ring carbon atoms by respectively, one or more substituents independently selected from ($C_1$–$C_6$)alkyl optionally substituted with one or more halo atoms, halo, nitro, cyano, —$(CH_2)_n$—$NR^7R^8$, —$(CH_2)_n$—$CO_2R^2$,

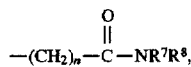

—$(CH_2)_n$—$(CH_2)_n$—$OR^2$, —$(CH_2)_n$—$SO_2R^2$, —$(CH_2)_n$—$SO_2$—($C_1$–$C_6$)alkyl, or —$(CH_2)_n$—$SO_2NR^7R^8$; wherein the phenylmoiety of said —$(CH_2)_n$-phenyl may optionally be substituted with one or more substituents, independently selected from ($C_1$–$C_6$)alkyl optionally substituted with one or more halo atoms, hydroxy, ($C_1$–$C_6$)alkoxy optionally substituted with one or more halo atoms, ($C_1$–$C_6$)alkylthio, fluoro, chloro, bromo, iodo, cyano, nitro, —$(CH_2)_n$—$NR^7R^8$, —$(CH_2)_n$—$CO_2R^2$.

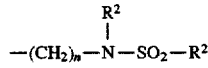

—$(CH_2)_n$—$OR^2$, —$(CH_2)_n$—$SO_3R^2$, —$(CH_2)_n$—$SO_2$—($C_1$–$C_6$)alkyl, —$(CH_2)_n$—$SO_2NR^7R^8$,

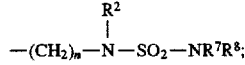

wherein each $R^2$ is selected in independently of the other $R^2$ and

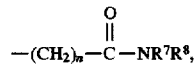

$R^4$ is —$(CH_2)_n$—CN, —$(CH_2)_n CO_2R^2$, —$(CH_2)_n$—$SO_3R^{21}$, —$(CH_2)_n$—$SO_2$—($C_1$–$C_6$)alkyl, —$(CH_2)_n$—$SO_2$—$NR^7R^8$, —$(CH_2)_n CH_2OH$ optionally substituted with a suitable protecting group, —$(CH_2)_n$—CHO, —$(CH_2)_n$—C(=O)$R^2$, —$(CH_2)_n$—C(=O)$NR^7R^8$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl; wherein one of the ring nitrogen atoms of said —$(CH_2)_n$-imidazolyl, —$(CH_2)_n$-triazolyl and —$(CH_2)_n$-tetrazolyl may optionally be substituted by ($C_1$–$C_6$)alkyl optionally substituted with one or more halo atoms; wherein each of said heterocycles may optionally be substituted on one or more of the ring carbon atoms by respectively, one or more substituents independently selected from hydrogen, ($C_1$–$C_6$)alkyl optionally substituted with one or more halo atoms, —$(CH_2)_n$-$NR^7R^8$, —$(CH_2)_n$—$CO_2R^2$, halo, nitro, cyano,

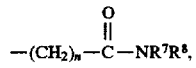

—$(CH_2)_nOR^2$, —$(CH_2)_n$-$SO_3R^2$, —$(CH_2)_n$—$SO_2$—($C_1$–$C_6$)alkyl, or —$(CH_2)_n$—$SO_2NR^7R^8$;

$R^5$ is hydrogen or ($C_1$–$C_6$)alkyl optionally substituted with one or more halo atoms;

$R^7$ and $R^8$ are independently hydrogen, ($C_{1-C_6}$)alkyl optionally substituted with one or more halo, ($C_1$–$C_8$) alkoxy($C_1$–$C_6$)alkyl or ($C_3$–$C_8$)cycloalkyl, or $R^7$ and $R^8$, together with the nitrogen to which they are attached, form a saturated heterocyclic ring having from 3 to 7 carbon atoms wherein one of said carbon atoms may optionally be replaced by oxygen, nitrogen or sulfur;

n is an integer from zero to six;

X is a direct link, oxygen or sulfur;

Y is nitrogen; and

Z is carbon; with the proviso that: (a) when Y is oxygen or sulfur, $R^3$ is absent, or a pharmaceutically acceptable pro-drug of such compound, or a pharmaceutically acceptable salt of such compound or pro-drug.

2. A compound according to claim 1, wherein $R^1$ is —$(CH_2)_n$—O-phenyl optionally substituted with one or more substituents independently selected from hydrogen, ($C_1$–$C_6$)alkyl optionally substituted with one or more halo atoms, hydroxy, ($C_1$–$C_6$)alkoxy, ($C_1$–$C_6$)alkylthio, amino, fluoro, chloro, bromo and iodo.

3. A compound according to claim 1, wherein $R^1$ is phenyl optionally substituted with one or more substituents independently selected from hydrogen, ($C_1$–$C_6$)alkyl optionally substituted with one or more halo atoms, hydroxy, ($C_1$–$C_6$) alkoxy optionally substituted with one or more halo atoms, ($C_1$–$C_6$)alkylthio, amino, fluoro, chloro, bromo and iodo.

4. A compound according to claim 1, wherein $R^1$ is pyridyl wherein one or more of the ring carbon atoms may independently be substituted with hydrogen, ($C_1$–$C_6$)alkyl optionally substituted with one or more halo atoms, hydroxy, ($C_1$–$C_6$)alkoxy optionally substituted with one or more halo atoms, ($C_1$–$C_6$)alkylthio, amino, fluoro, chloro, bromo and iodo.

5. A compound according to claim 1 wherein $R^1$ is phenyl, —$(CH_2)$—O-phenyl or pyridyl; wherein said phenyl and the phenyl moiety of said —$(CH_2)_n$—O-phenyl may optionally be substituted with one or more substituents; wherein one or more of the carbon atoms of said pyridyl may optionally be substituted; and wherein said substituents are optionally halogen, amino or hydroxy.

6. A compound according to claim 1, wherein x is oxygen.

7. A compound according to claim 2, wherein X is oxygen.

8. A compound according to claim 3, wherein X is oxygen.

9. A compound according to claim 4, wherein X is oxygen.

10. A compound according to claim 5, wherein X is oxygen.

11. A compound according to claim 1, wherein X is a direct link.

12. A compound according to claim 2, wherein X is a direct link.

13. A compound according to claim 3, wherein X is a direct link.

14. A compound according to claim 4, wherein X is a direct link.

15. A compound according to claim 5, wherein X is a direct link.

16. A compound according to claim 6, wherein $R^4$ is —$CO_2CH_3$, —$CO_2H$, —C(=O)$CH_3$, nitrile (—C≡N), or a heterocycle selected from 3-1,2,4-oxadiazolyl, 5-methyl-1,2,4-oxadiazolyl, 3-isoxazolyl, 3-5-methyl-isoxazolyl, 4-(2-methyl(thiazolyl)), 3-methyl-1,2,4-oxadiazolyl and 5-1,2,4-oxadiazolyl.

17. A compound according to claim 1, wherein $R^4$ is —$CO_2R^2$.

18. A compound according to claim 13, wherein $R^4$ is —$CO_2R^2$.

19. A compound according to claim 1, wherein Y is nitrogen.

20. A compound according to claim 2, wherein Y is nitrogen.

21. A compound according to claim 3, wherein Y is nitrogen.

22. A compound according to claim 4, wherein Y is nitrogen.

23. A compound according to claim 10, wherein Y is nitrogen.

24. A compound according to claim 11, wherein Y is nitrogen.

25. A compound according to claim 12, wherein Y is nitrogen.

26. A compound according to claim 13, wherein Y is nitrogen.

27. A compound according to claim 16, wherein Y is nitrogen.

28. A compound according to claim 12, wherein Y is nitrogen and $R^3$ is hydrogen, methyl, ethyl, phenylmethyl, pyridylmethyl, pyrizinylmethyl or pyrimidyl-methyl.

29. A compound according to claim 1 wherein $R^3$ is hydrogen, methyl, ethyl, phenylmethyl, pyrimidylmethyl, pyrizinylmethyl or pyridiylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by —$SO_2$—$NR^7R^8$,

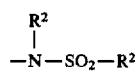

wherein each $R^2$ is selected independently of the other $R^2$ and

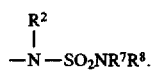

30. A compound according to claim 18 wherein $R^3$ is hydrogen, methyl, ethyl, phenylmethyl, pyrimidylmethyl, pyrizinylmethyl or pyridinylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by —$SO_2$—$NR^7R^8$,

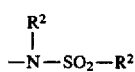

wherein each $R^2$ is selected independently of the other $R^2$ and

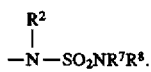

31. A compound according to claim 19 wherein $R^3$ is hydrogen, methyl, ethyl, phenylmethyl, pyrimidylmethyl, pyrizinylmethyl or pyridinylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by —$SO_2$—$NR^7R^8$,

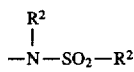

wherein each $R^2$ is selected independently of the other $R^2$ and

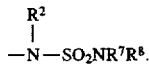

32. A compound according to claim 20 wherein $R^3$ is hydrogen, methyl, ethyl, phenylmethyl, pyrimidylmethyl, pyrizinylmethyl or pyridinylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by —$SO_2$—$NR^7R^8$.

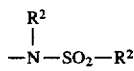

wherein each $R^2$ is selected independently of the other $R^2$ and

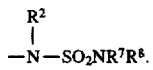

33. A compound according to claim 21 wherein $R^3$ is hydrogen, methyl, ethyl, phenylmethyl, pyrimidylmethyl, pyrizinylmethyl or pyridinylmethyl wherein each of said phenyl, pyrimidyl, pyrizinyl or pyridinyl moieties of said phenylmethyl, pyrimidylmethyl, pyrizinylmethyl, or pyridinylmethyl groups may optionally be substituted by —$SO_2$—$NR^7R^8$.

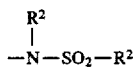

wherein each $R^2$ is selected independently of the other $R^2$ and

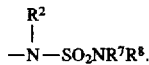

34. A compound according to claim 1, wherein said compound is 1-benzyl-5-(2(R)-(2-(3-chloro-phenyl)-2(R)-hydroxy-ethylamino)-propyl)-1H-indole-2-carboxylic acid methyl ester, hydrochloride salt.

35. A compound according to claim 1, wherein said compound is 1-benzyl-5-(2(R)-(2-(3-chloro-phenyl)-2(R)-hydroxy-ethylamino)-propyl)-1H-indole-2-carboxylic acid.

36. A compound according to claim 1, wherein said compound is 1-benzyl-5-(2(R,S)-(2(S)-hydroxy-3-phenoxy-propylamino)-propyl)-1H-indole-2-carboxylic acid ethyl ester.

37. A compound according to claim 1, wherein said compound is 1-benzyl-5-(2(R,S)-(2S)-hydroxy-3-phenoxy-propylamino)-propyl)-1H-indole-2-carboxylic acid.

38. A compound according to claim 1, wherein said compound is 5-(2(R,S)-(2-(3-chloro-phenyl)-2(R)-hydroxy-ethylamino)-propyl)-1-(4dimethylsulfamoyl-benzyl)-1H-indole-2-carboxylic acid ethyl ester.

39. A compound according to claim 1, wherein said compound is 5-(2-(R,S)(2-(3-chloro-phenyl)-2(R)-hydroxy-ethylamino)-propyl)-1-(4-dimethylsulfamoyl-benzyl)-1H-indole-2-carboxylic acid.

40. A compound according to claim 1, wherein said compound is 1-(4-dimethylsuffamoyl-benzyl)-5-(2(R,S)-(2(S)-hydroxy-3-phenoxy-propylamino)-propyl)-1H-indole-2-carboxylic acid ethyl ester.

41. A compound according to claim 1, wherein said compound is 1-(4-dimethylsulfamoyl-benzyl)-5-(2(R,S)-(2(S)-hydroxy-3-phenoxy-propylamino)-propyl)-1H-indole-2-carboxylic acid.

42. A compound according to claim 1, wherein said compound is 5-(2(R,S)-(2-(3-chloro-phenyl)-2(R)-hydroxy-ethylamino)-propyl)-1-(4-methanesulfonylamino-benzyl)-1H-indole-2-carboxylic acid ethyl ester, hydrochloride salt.

43. A compound according to claim 1, wherein said compound is 5-(2(R,S)-(2-(3-chloro-phenyl)-2(R)-hydroxy-ethylamino)-propyl)-1-(4-methanesulfonylamino-benzyl)-1H-indole-2-carboxylic acid.

44. A compound according to claim 1, wherein said compound is 5-(2(R.S)-(2(S)-hydroxy-3-phenoxy-propylamino)-propyl)-1-(4-methanesulfonylamino-benzyl)-1H-indole-2-carboxylic acid ethyl ester, hydrochloride salt.

45. A compound according to claim 1, wherein said compound is 5-(2(R,S)-(2(S)-hydroxy-3-phenoxy-propylamino)-propyl)-1-(4-methanesulfonylamino-benzyl)-1H-indole-2-carboxylic acid.

46. A compound according to claim 1, wherein said compound is 5-(2(R,S)-(2(R,S)-(6-amino-pyridin-3-yl)-2-hydroxy-ethylamino)-propyl)-1-benzyl-1H-indole-2-carboxylic acid ethyl ester.

47. A compound according to claim 1, wherein said compound is 5-(2(R,S)-(2(R,S)-(6-amino-pyridin-3-yl)-2-hydroxy-ethylamino)-propyl)-1-benzyl-1H-indole-2-carboxylic acid hydrochloride salt.

48. A pharmaceutical composition for treating a condition selected from the group consisting of diabetes, hyperglycemia and obesity in a mammal, comprising an amount of a compound according to claim 1 effective in treating such condition and a pharmaceutically acceptable carrier.

49. A method of treating a condition selected from the group consisting of diabetes, hyperglycemia and obesity in a mammal, comprising administering to a mammal in need of such treatment an amount of a compound according to claim 1 effective in treating such condition.

50. A pharmaceutical composition for treating a condition selected from the group consisting of diabetes, hyperglycemia and obesity in a mammal, comprising a $\beta_3$-adrenoceptor stimulating amount of a compound according to claim 1 and a pharmaceutically acceptable carrier.

51. A method of treating a condition selected from the group consisting of diabetes, hyperglycemia and obesity in a mammal, comprising administering to a mammal in need of such treatment a $\beta_3$-adrenoceptor stimulating amount of a compound according to claim 1.

52. A pharmaceutical composition for increasing the content of lean meat in edible animals, comprising a $\beta_3$-adrenoceptor stimulating amount of a compound according to claim 1 and a pharmaceutically acceptable carrier.

* * * * *